(12) United States Patent
Fujita et al.

(10) Patent No.: US 12,161,444 B2
(45) Date of Patent: Dec. 10, 2024

(54) HEALTH DEVICE FLOW PATH FORMATION MEMBER, HEALTH DEVICE FLOW PATH FORMATION UNIT, AND HEALTH DEVICE

(71) Applicants: OMRON HEALTHCARE Co., Ltd., Kyoto (JP); OMRON Corporation, Kyoto (JP)

(72) Inventors: Reiji Fujita, Kyoto (JP); Yasuhiro Kawabata, Kyoto (JP)

(73) Assignees: OMRON CORPORATION, Kyoto (JP); OMRON HEALTHCARE CO., LTD., Kyoto (JP)

( * ) Notice: Subject to any disclaimer, the term of this patent is extended or adjusted under 35 U.S.C. 154(b) by 593 days.

(21) Appl. No.: 16/813,988

(22) Filed: Mar. 10, 2020

(65) Prior Publication Data

US 2020/0205679 A1    Jul. 2, 2020

Related U.S. Application Data

(63) Continuation of application No. PCT/JP2018/030526, filed on Aug. 17, 2018.

(30) Foreign Application Priority Data

Sep. 14, 2017   (JP) .................................. 2017-176933

(51) Int. Cl.
 *A61B 5/021* (2006.01)
 *A61B 5/00* (2006.01)
(52) U.S. Cl.
 CPC ...... *A61B 5/02141* (2013.01); *A61B 5/02116* (2013.01); *A61B 5/02125* (2013.01); *A61B 5/681* (2013.01); *A61B 2560/02* (2013.01)
(58) Field of Classification Search
 CPC ............ A61B 5/02141; A61B 5/02116; A61B 5/02125; A61B 5/681; A61B 2560/02; A61B 5/022
See application file for complete search history.

(56) References Cited

U.S. PATENT DOCUMENTS

| 2005/0282290 A1 | 12/2005 | Fujimoto et al. |
| 2006/0292039 A1 | 12/2006 | Iida |

(Continued)

FOREIGN PATENT DOCUMENTS

| JP | H09101220 A | 4/1997 |
| JP | 2009-178951 | 8/2009 |

(Continued)

OTHER PUBLICATIONS

International Search Report of the International Searching Authority for PCT/JP2018/030526 with mailing date of Oct. 9, 2018.

(Continued)

*Primary Examiner* — Yi-Shan Yang
*Assistant Examiner* — Joseph A Tombers
(74) *Attorney, Agent, or Firm* — Wenderoth, Lind & Ponack, L.L.P.

(57) ABSTRACT

A health device flow path formation member (500) includes a flow path (604) configured to supply fluid to a target supply member, a first opening portion (601) located at a first end of the flow path, a second opening portion (602) located at a second end of the flow path, a connection path (603), a plate-like member (610) including the connection path (603), and a joining layer (620) including the first opening portion (601), the joining layer (620) joining the plate-like member (610) to a first target attachment member (32) with the first opening portion (601) communicating with a fluid path (32a) of the first target attachment member (32). When viewed in a first direction in which the joining layer (620) and the plate-like member (610) overlap, the first opening portion (610) is disposed inward a distance from a profile line of a projection of the connection path (603) in the first direction, forming a first protrusion portion in the joining layer (620) that protrudes inward from the profile line.

11 Claims, 16 Drawing Sheets

(56) References Cited

U.S. PATENT DOCUMENTS

| | | |
|---|---|---|
| 2009/0054794 A1 | 2/2009 | Shirasaki |
| 2009/0195606 A1 | 8/2009 | Hirasawa et al. |
| 2010/0076328 A1 | 3/2010 | Matsumura et al. |
| 2010/0079546 A1 | 4/2010 | Takahashi |
| 2011/0112412 A1* | 5/2011 | Sano ................. A61B 5/02233 600/499 |
| 2014/0087479 A1 | 3/2014 | Albuquerque et al. |
| 2014/0296891 A1 | 10/2014 | Kojima et al. |
| 2017/0215744 A1* | 8/2017 | Kawamura .......... A61B 5/0235 |
| 2018/0132738 A1 | 5/2018 | Choi et al. |
| 2019/0343405 A1* | 11/2019 | Tanaka ................... F04B 41/02 |

FOREIGN PATENT DOCUMENTS

| | | |
|---|---|---|
| JP | 2010-105391 | 5/2010 |
| JP | 2014-515822 A | 7/2014 |
| JP | 2014188239 A | 10/2014 |
| KR | 10-2016-0127641 | 11/2016 |
| WO | 2003/093836 A1 | 11/2003 |
| WO | WO2005024437 A1 | 3/2005 |
| WO | WO2008065873 A1 | 6/2008 |
| WO | WO2016063710 A1 | 4/2016 |

OTHER PUBLICATIONS

Translation of the International Search Report of the International Searching Authority for PCT/JP2018/030526 with mailing date of Oct. 9, 2018.

Office Action issued Feb. 14, 2022 in corresponding Chinese Patent Application No. 201880058359.0, with English-language translation.

Decision to Grant Patent issued May 18, 2021 in corresponding Japanese Patent Application No. 2017-176933, with English translation.

International Search Report of the International Searching Authority for PCT/JP2018/030411 with mailing date of Oct. 9, 2018.

Translation of the International Search Report of the International Searching Authority for PCT/JP2018/030411 with mailing date of Oct. 9, 2018.

International Preliminary Report on Patentability (Chapter II) of the International Preliminary Examining Authority for PCT/JP2018/030526 with search date of May 27, 2019.

English translation of International Preliminary Report on Patentability (Chapter II) of the International Preliminary Examining Authority for PCT/JP2018/030526 with search date of May 27, 2019.

* cited by examiner

HEALTH DEVICE FLOW PATH FORMATION MEMBER, HEALTH DEVICE FLOW PATH FORMATION UNIT, AND HEALTH DEVICE

CROSS-REFERENCE TO RELATED APPLICATIONS

This is a continuation of International Application JP 2017-176933 filed on Sep. 14, 2017 and also PCT/JP2018/030526 with an international filing date of Aug. 17, 2018, filed by applicant, the disclosure of which is hereby incorporated by reference in its entirety.

TECHNICAL FIELD

The present invention relates to a health device flow path formation member for supplying fluid to a target supply member, and a health device flow path formation unit and a health device including the same.

BACKGROUND ART

An example of a known health device flow path formation member includes that described in JP 2014-188239 A (Patent Document 1). Patent Document 1 describes a health device flow path formation member that includes a connection tube that connects together a fluid supply source and a handpiece (target supply member).

CITATION LIST

Patent Literature

Patent Document 1: JP 2014-188239 A

SUMMARY OF INVENTION

Technical Problem

A configuration that uses a connection tube to connect together a fluid supply source and a target supply member to which fluid is supplied, typically includes an insertion portion at both the fluid supply source and the target supply member, the insertion portion being where an end of the connection tube is engaged. The insertion portion is configured as a cylindrical nozzle, and thus has a substantial length.

In a configuration in which the insertion portion of the fluid supply source and the insertion portion of the target supply member are formed not straight, when the end of the connection tube is engaged with the insertion portion, the end of the connection tube bends, making a change in the direction of the flow path. As a result, the health device flow path formation unit includes the fluid supply source, the target supply member, and the connection tube that connects the fluid supply source and the target supply member and is formed relatively thick to conform to the length of the insertion portion and the thickness of the bend portion of the connection tube. As a result, the thickness of the health device including the health device flow path formation unit increases.

In a configuration in which the health device flow path formation unit described above is reduced in size by shortening the length of the insertion portion, the engagement of the connection tube becomes loose and air tightness decreases. Thus, using a connection tube as a flow path formation member makes it difficult to reduce the size of a health device including the connection tube while also maintaining good air tightness.

The present invention has been made in view of the problems described above, and an object of the present invention is to provide a health device flow path formation member that can be included in compact health devices and has excellent air tightness and a health device flow path formation unit and a health device including the same.

Solution to Problem

A health device flow path formation member according to an embodiment of the present disclosure includes:
a flow path configured to supply fluid to a target supply member;
a first opening portion located at a first end of the flow path;
a second opening portion located at a second end of the flow path;
a connection path connecting the first opening portion and the second opening portion;
a plate-like member including the connection path; and
a joining layer including at least the first opening portion of the first opening portion and the second opening portion, the joining layer joining the plate-like member to a first target attachment member with the first opening portion communicating with a fluid path of the first target attachment member. When viewed in a first direction in which the joining layer and the plate-like member overlap, the first opening portion is disposed inward a distance from a profile line of a projection of the connection path in the first direction, forming a first protrusion portion in the joining layer that protrudes inward from the profile line.

In the health device flow path formation member according to an embodiment of the present disclosure described above, the connection path may include a main path portion provided inside the plate-like member, a first auxiliary path portion connecting the first opening portion and the main path portion, and a second auxiliary path portion connecting the second opening portion and the main path portion. In this embodiment, when viewed in the first direction, the first auxiliary path portion is preferably disposed inward from the main path portion, forming a first projection portion in the plate-like member that defines the first auxiliary path portion and projects inward from the main path portion; and
the first protrusion portion is preferably supported by the first projection portion.

In the health device flow path formation member according to an embodiment of the present disclosure described above, the second opening portion may be disposed in the joining layer.

In the health device flow path formation member according to an embodiment of the present disclosure described above, when viewed in the first direction, the second opening portion may be disposed inward a distance from the profile line of the projection, forming a second protrusion portion in the joining layer that protrudes inward from the profile line.

The health device flow path formation member according to an embodiment of the present disclosure described above may further include a connection layer including the second opening portion, the connection layer connecting the plate-like member to a second target attachment member with the second opening portion communicating with a fluid path of the second target attachment member. In this embodiment, the plate-like member preferably includes a first main surface and a second main surface that are front and back surfaces in the first direction. Also, the joining layer is preferably disposed on a side of the plate-like member where the first main surface is located, and the connection layer is preferably disposed on a side of the plate-like member where the second main surface is located.

In the health device flow path formation member according to an embodiment of the present disclosure described above, when viewed in the first direction, the second opening portion is preferably disposed inward a distance from the profile line of the projection of the connection path in the first direction, forming a second protrusion portion in the connection layer that protrudes inward from the profile line.

In the health device flow path formation member according to an embodiment of the present disclosure described above, wherein the connection path preferably includes a tapered portion at a portion located at the first end, the tapered portion tapering becoming thinner in the first direction in a direction away from the joining layer.

A health device flow path formation unit according to an embodiment of the present disclosure includes:

the health device flow path formation member described above; and the first target attachment member on which the health device flow path formation member is attached.

In the health device flow path formation unit according to an embodiment of the present disclosure described above, the first target attachment member preferably includes a first target attachment surface on which the health device flow path formation member is attached. In this embodiment, the first target attachment surface preferably includes a groove portion provided around the first opening portion in a region overlapping the first protrusion portion when viewed in the first direction, the groove portion being recessed in a direction away from the health device flow path formation member in the first direction.

In the health device flow path formation unit according to an embodiment of the present disclosure described above, the first target attachment member is preferably a fluid supply source that supplies fluid.

The health device flow path formation unit according to an embodiment of the present disclosure described above preferably further includes the second target attachment member on which the health device flow path formation member is attached, with the second opening portion communicating with the fluid path of the second target attachment member.

In the health device flow path formation unit according to an embodiment of the present disclosure described above, the second target attachment member is preferably a connection member through which fluid is supplied from the health device flow path formation member to a target supply member.

A health device according to an embodiment of the present disclosure includes:

the health device flow path formation unit; and a fluid bag into which fluid is supplied from the health device flow path formation unit.

Advantageous Effects of Invention

The present invention can provide a health device flow path formation member that can be included in compact health devices and has excellent air tightness and a health device flow path formation unit and a health device including the same.

DESCRIPTION OF EMBODIMENTS

Figure 1:
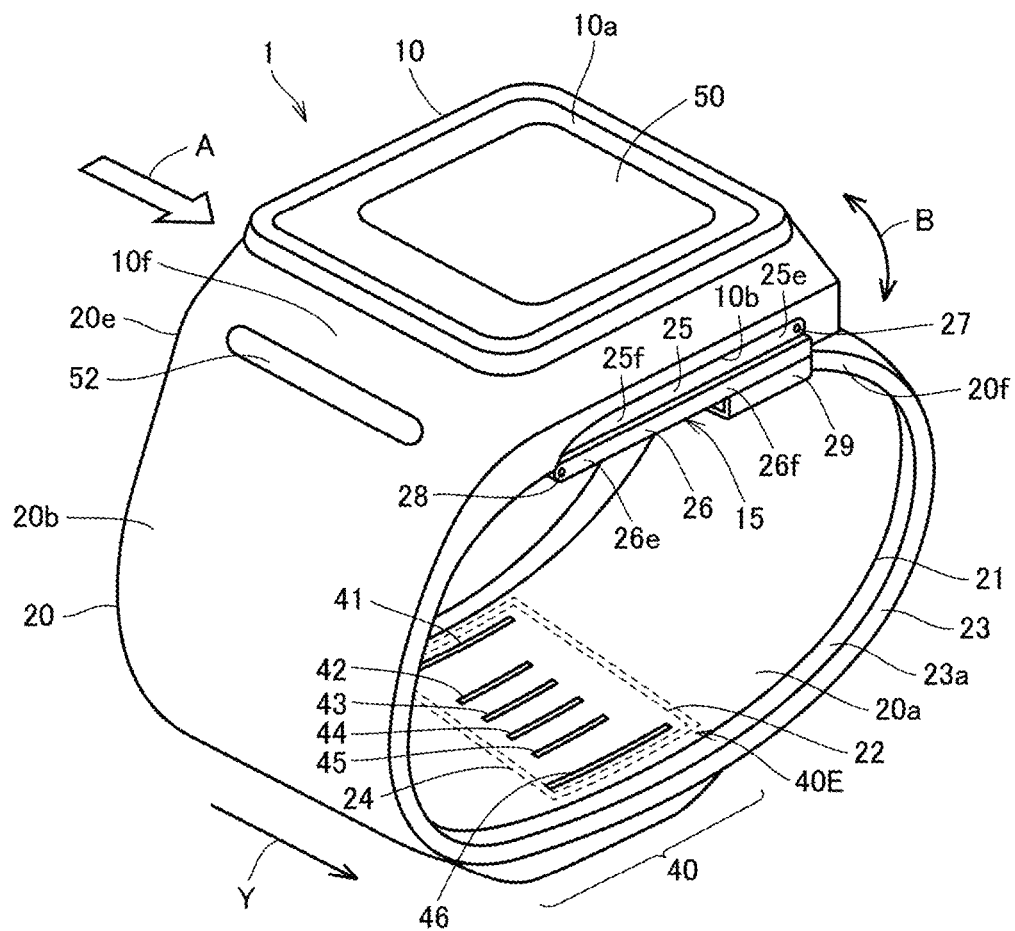
FIG. 1 is a perspective view illustrating an appearance of a wrist blood pressure monitor according to a first embodiment.

Embodiments of the present invention will be described in detail below with reference to the drawings. Note that in the following embodiments, identical or common components are given the same reference signs in the drawings, and the descriptions thereof are not repeated.

Also, in the following embodiments, a wrist blood pressure monitor is used as an example of a health device, but the health device is not limited to being a wrist blood pressure monitor and can also be applied to other health devices that have a configuration in which a fluid bag is expanded and contracted by the supply and discharge of a fluid.

First Embodiment

Figure 2:
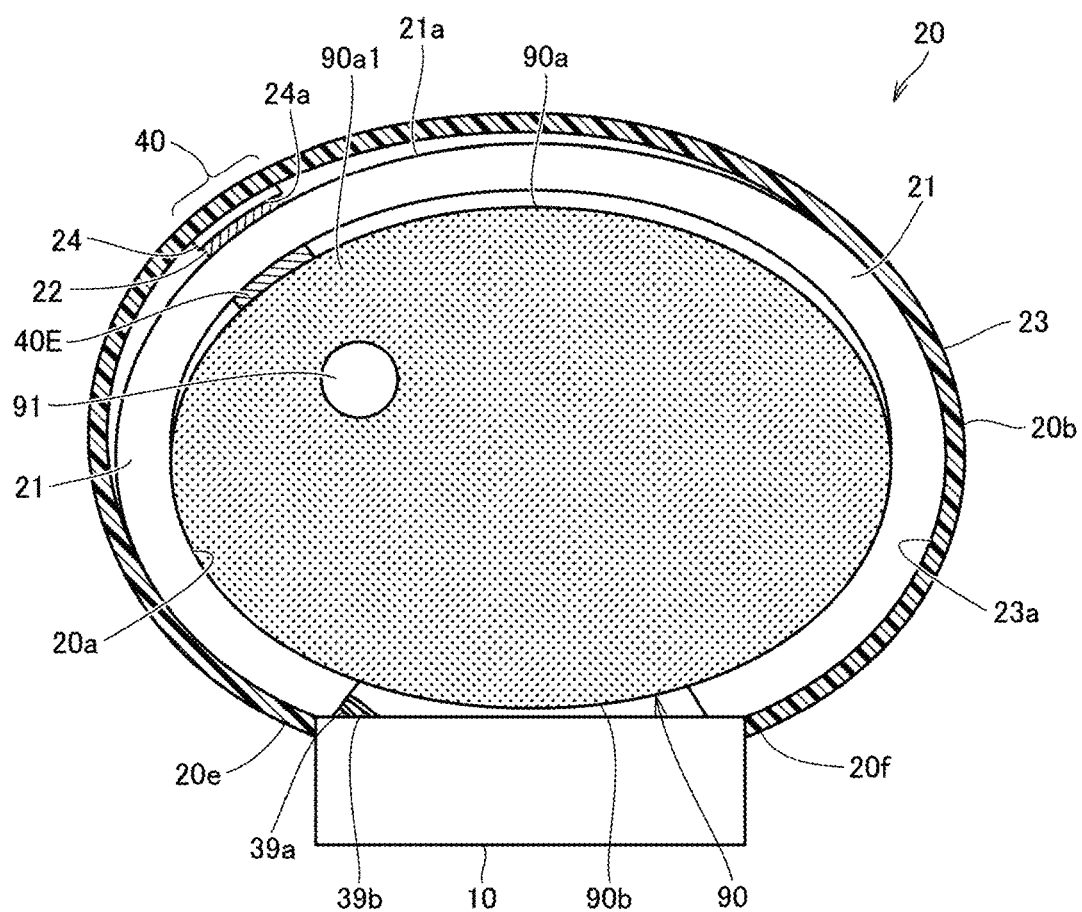
FIG. 2 is a diagram schematically illustrating the wrist blood pressure monitor according to the first embodiment in a cross section perpendicular to the longitudinal direction of the wrist, the wrist blood pressure monitor being worn on the left wrist.

FIG. 1 is a perspective view illustrating an appearance of a wrist blood pressure monitor according to a first embodiment. FIG. 2 is a diagram schematically illustrating the wrist blood pressure monitor according to the first embodiment in a cross section perpendicular to the longitudinal direction of the wrist, the wrist blood pressure monitor being worn on the left wrist.

As illustrated in FIGS. 1 and 2, a wrist blood pressure monitor 1 (referred to as simply blood pressure monitor 1 below) mainly includes a belt 20 worn around a left wrist 90 of the user and a body 10 integrally attached to the belt 20.

The belt 20 has an elongated band-like shape allowing it to wrap around the left wrist 90 in the circumferential direction. The dimension (width dimension) of the belt 20 in a width direction Y is, for example, approximately 30 mm. The belt 20 includes a band 23 that constitutes an outer circumferential surface 20b and a compression cuff 21 attached and conforming to an inner circumferential surface 23a of the band 23. The compression cuff 21 is a first fluid bag that constitutes an inner circumferential surface 20a that comes into contact with the left wrist 90. The compression cuff 21, like the belt 20, has an elongated band-like shape allowing it to wrap around the left wrist 90 in the circumferential direction.

The body 10 is integrally formed with the belt 20 at one end portion 20e in the circumferential direction via integral forming, for example. Note that the belt 20 and the body 10 may be formed separately, and the body 10 may be integrally attached to the belt 20 using an engagement member such as a hinge.

As illustrated in FIG. 2, the location where the body 10 is disposed corresponds to a back side surface (surface on the back side of the hand) 90b of the left wrist 90 when the device is worn. A radial artery 91 runs through the left wrist 90 near a palm side surface 90a (surface on the palm side of the hand).

Returning to FIG. 1, the body 10 has a thickness in the direction perpendicular to the outer circumferential surface 20b of the belt 20. The body 10 is formed compact and thin, so as to not interfere with the daily activities of the user. The body 10 has a truncated quadrangular pyramid profile protruding outward from the belt 20.

A display 50 including a display screen is provided on a top surface (surface on the far side from the target measurement site) 10a of the body 10. Also, an operation portion 52 is provided along a side surface (side surface on the left front side in FIG. 1) 10f of the body 10. The operation portion 52 is for the input of instructions from the user.

The belt 20 is provided with an impedance measurement portion 40 on the inner circumferential surface 20a of the compression cuff 21, which constitutes the inner circumferential surface 20a of the belt 20, at a portion in the circumferential direction between the end portion 20e and another end portion 20f. The impedance measurement portion 40 constitutes a first pulse wave sensor and a second pulse wave sensor.

The belt 20 is provided with six plate-like (sheet-like) electrodes 41 to 46 (referred to collectively as "electrode group 40E" below) at the inner circumferential surface 20a where the impedance measurement portion 40 is disposed. The electrodes 41 to 46 are separated from each other in the width direction Y of the belt 20. The location where the electrode group 40E is disposed corresponds to the radial artery 91 (see FIG. 2) of the left wrist 90 when the device is worn.

As illustrated in FIG. 2, a solid material 22 is disposed on an outer circumferential surface 21a that is on the opposite side of the inner circumferential surface 20a of the compression cuff 21 where the electrode group 40E is disposed. The solid material 22 is disposed at a position corresponding to the electrode group 40E. Also, a pressing cuff 24 is disposed on the outer circumference side of the solid material 22. The pressing cuff 22 is an expandable member that locally presses against a region in the circumferential direction of the compression cuff 21 corresponding to the electrode group 40E. The pressing cuff 24 corresponds to a second fluid bag.

The pressing cuff 24 is disposed on the inner circumferential surface 23a of the band 23 constituting the belt 20 (see FIG. 2). The pressing cuff 24 is a fluid bag that expands and contracts in the thickness direction of the belt 20. The pressing cuff 24 is put in a pressurized state when fluid is supplied and in a non-pressurized state when fluid is discharged.

As illustrated in FIG. 1, a bottom surface (surface on the near side to the target measurement site) 10b of the body 10 and the end portion 20f of the belt 20 are connected via a tri-fold buckle 15. The buckle 15 includes a first plate-like member 25 disposed on the outer circumference side and a second plate-like member 26 disposed on the inner circumference side.

A first end portion 25e of the first plate-like member 25 is attached in a freely rotatable manner to the body 10 via a connecting rod 27 that extends in the width direction Y. A second end portion 25f of the first plate-like member 25 is attached in a freely rotatable manner to a first end portion 26e of the second plate-like member 26 via a connecting rod 28 that extends in the width direction Y. A second end portion 26f of the second plate-like member 26 is fixed at a position near the end portion 20f of the belt 20 via a fixing portion 29.

Note that the attachment position of the fixing portion 29 in the circumferential direction of the belt 20 is set in advance in accordance with the circumference length of the left wrist 90 of the user. Thus, the blood pressure monitor 1 (belt 20) is formed in an overall substantially annular shape, and the buckle 15 can open and close in the arrow B direction to separate and bring together the bottom surface 10b of the body 10 and the end portion 20f of the belt 20.

When the blood pressure monitor 1 is worn on the left wrist 90, the buckle 15 is opened to increase the annular diameter of the belt 20 and the user puts their left hand through the belt 20 in the arrow A direction illustrated in FIG. 1. Then, as illustrated in FIG. 2, the user adjusts the angular position of the belt 20 around the left wrist 90 and positions the impedance measurement portion 40 of the belt 20 above the radial artery 91 running through the left wrist 90. This bring the electrode group 40E of the impedance measurement portion 40 into contact with a portion 90a1 of the palm side surface 90a of the left wrist 90 corresponding to the radial artery 91. In this way, the user wears the blood pressure monitor 1 (belt 20) on the left wrist 90.

As illustrated in FIG. 2, the band 23 has flexibility in the thickness direction and is made of a plastic material that is substantially non-stretchable in the circumferential direction (longitudinal direction). The compression cuff 21 is formed by, for example, welding together edge portions of two stretchable polyurethane sheets layered in the thickness direction. As described above, the electrode group 40E of the impedance measurement portion 40 is disposed at a position on the inner circumferential surface 20a of the compression cuff 21 (belt 20) corresponding to the radial artery 91 of the left wrist 90.

Figure 3:
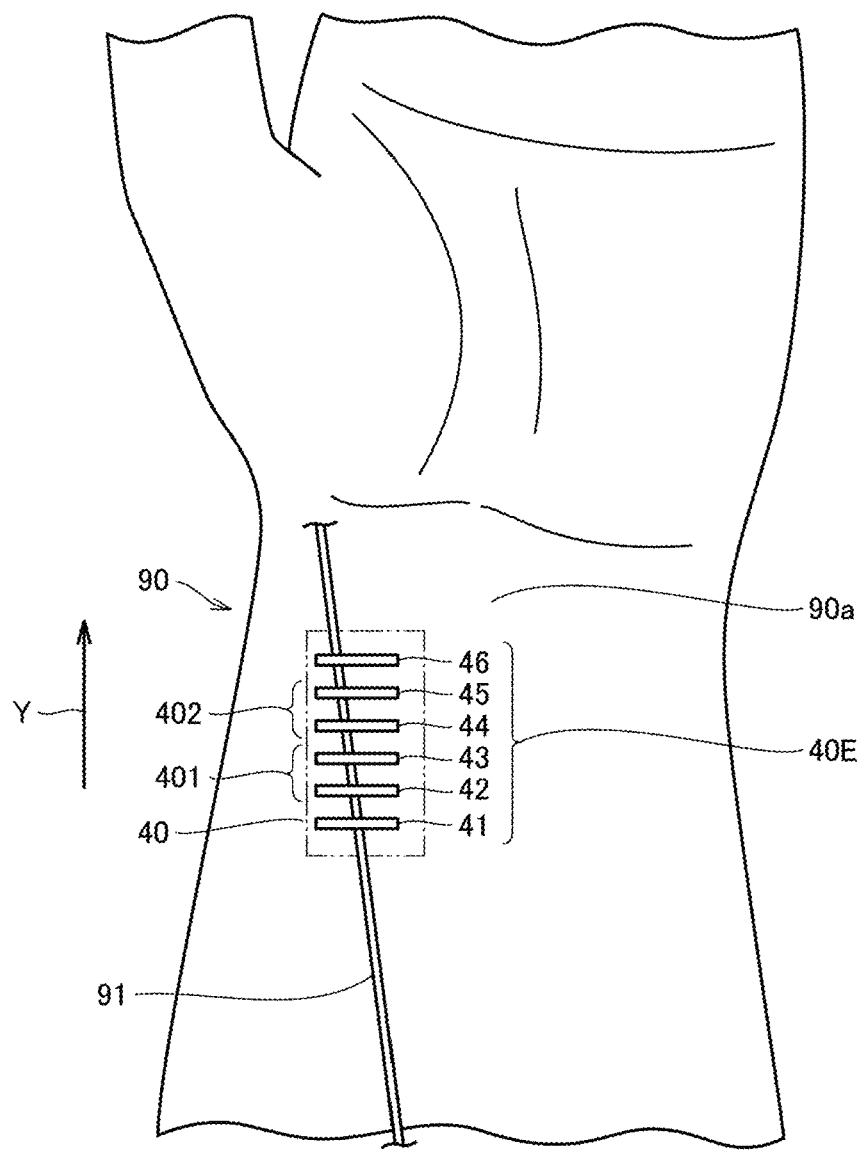
FIG. 3 is a plan view of the layout of an impedance measurement electrode that constitutes a first pulse wave sensor and a second pulse wave sensor when the wrist blood pressure monitor according to the first embodiment is worn on the left wrist.

FIG. 3 is a plan view of the layout of an impedance measurement electrode that constitutes the first pulse wave sensor and the second pulse wave sensor when the wrist blood pressure monitor 1 according to the first embodiment is worn on the left wrist.

As illustrated in FIG. 3, when the device is worn, the electrodes of the electrode group 40E of the impedance measurement portion 40 are arranged side by side in the longitudinal direction of the wrist (the width direction Y of the belt 20) following the radial artery 91 of the left wrist 90. The electrode group 40E includes a current-conducting current electrode pair 41, 46 disposed on either side in the width direction Y, a first detection electrode pair 42, 43 that constitutes a first pulse wave sensor 401, and a second detection electrode pair 44, 45 that constitutes a second pulse wave sensor 402.

The first pulse wave sensor 401 and the second pulse wave sensor 402 are disposed between the current electrode pair 41, 46. The first detection electrode pair 42, 43 and the second detection electrode pair 44, 45 are both voltage-detection electrodes.

The second detection electrode pair 44, 45 is disposed downstream of the first detection electrode pair 42, 43 in the blood flow direction of the radial artery 91. A distance D (see FIG. 5A) in the width direction Y between a central point between the first detection electrode pair 42, 43 and a central point between the second detection electrode pair 44, 45 is approximately 20 mm, for example. The distance D corresponds to the actual interval between the first pulse wave sensor 401 and the second pulse wave sensor 402. Furthermore, the interval in the width direction Y between the first detection electrode pair 42, 43 is approximately 2 mm, and the interval in the width direction Y between the second detection electrode pair 44, 45 is approximately 2 mm, for example.

The electrode group 40E can have a flat configuration. Thus, the belt 20 of the blood pressure monitor 1 can have an overall thin configuration. Also, the electrode group 40E can have a flexible configuration. Thus, the electrode group 40E does not interfere with the compression of the left wrist 90 by the compression cuff 21, preventing a decrease in the precision of the blood pressure measurement performed via the oscillometric method described below.

Returning to FIG. 2, the pressing cuff 24, i.e., expandable member, is disposed on the inner circumferential surface 23a of the band 23 that constitutes the belt 20, as described above. The pressing cuff 24 includes a fluid bag, for example. The pressing cuff 24 is formed by welding together edge portions of two stretchable polyurethane sheets layered in the thickness direction. The solid material 22 is disposed on an inner circumferential surface 24a of the pressing cuff 24 at a position corresponding to the electrode group 40E. The solid material 22 is made of resin formed in a plate-like shape with a thickness from approximately 1 mm to 2 mm, for example. The solid material 22 is made of a polypropylene resin, for example. The pressing portion according to the present embodiment includes the belt 20, the pressing cuff 24, and the solid material 22.

Figure 4:
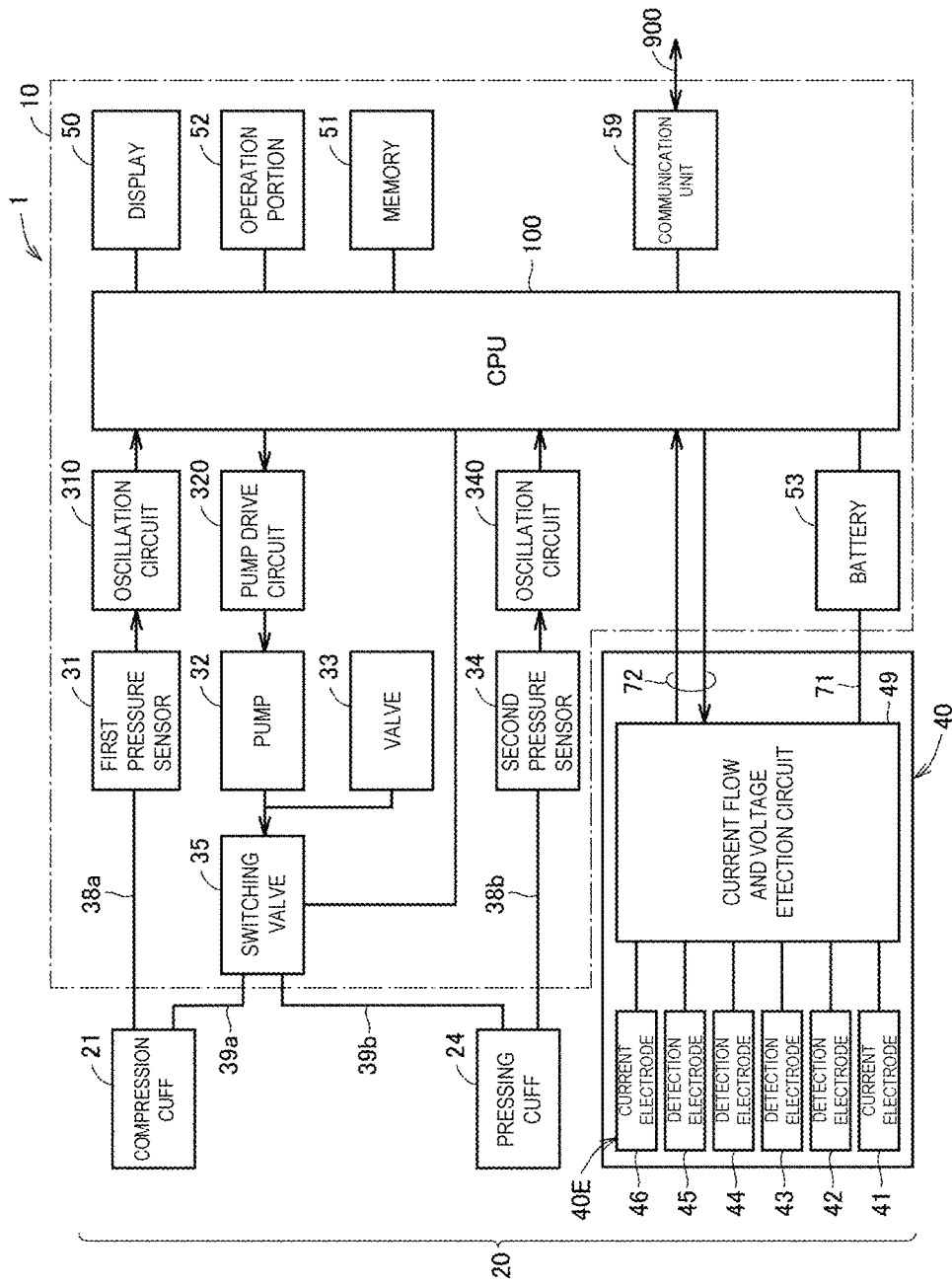
FIG. 4 is a block diagram illustrating the control configuration of the wrist blood pressure monitor according to the first embodiment.

FIG. 4 is a block diagram illustrating the control configuration of the wrist blood pressure monitor according to the first embodiment. Referring to FIG. 4, the control configuration of the blood pressure monitor 1 will be described.

As illustrated in FIG. 4, the display 50 and the operation portion 52 described above and a CPU 100, i.e., control unit, a memory 51, i.e., a storage unit, and a communication unit 59 are disposed in the body 10 of the blood pressure monitor 1. Also, a first pressure sensor 31, a pump 32, i.e., a fluid supply source, a valve 33, and a second pressure sensor 34 are disposed in the body 10. Also, an oscillation circuit 310 and an oscillation circuit 340 that convert the output of the first pressure sensor 31 and the second pressure sensor 34, respectively, into a frequency and a pump drive circuit 320 that drives the pump 32 are disposed in the body 10. Also, the electrode group 40E described above and a current flow and voltage detection circuit 49 are disposed in the impedance measurement portion 40. Also, a switching valve 35 for switching the connection destination of the pump 32 and the valve 33 between the compression cuff 21 and the pressing cuff 24 is provided. Also, a health device flow path formation unit 500 (see FIG. 5A) is disposed in the body 10 of the blood pressure monitor 1. The health device flow path formation unit 500, as described below, includes a health device flow path formation member 600, the pump 32, and a connection member 700.

The display 50 includes an organic EL display, for example. The display 50 displays information relating to blood pressure measurement such as blood pressure measurement results and other information in accordance with a control signal from the CPU 100. Note that the display 50 is not limited to being an organic EL display and may be another type of display such as a liquid crystal display.

The operation portion 52 includes, for example, a push type switch and inputs to the CPU 100 an operation signal in response to an instruction from the user to start or stop blood pressure measurement. Note that the operation portion 52 is not limited to being a push type switch and may be, for example, a pressure sensitive type (resistance type) or a proximity type (capacitance type) touch panel type switch. Also, a microphone (not illustrated) may be provided for input of a start blood pressure measurement instruction from the user via sound.

The memory 51 non-transitorily stores data of a program for controlling the blood pressure monitor 1, data used to control the blood pressure monitor 1, settings data for setting various functions of the blood pressure monitor 1, data of measurement results of blood pressure values, and the like. Also, the memory 51 is used as working memory and the like for executing a program.

The CPU 100 executes various functions as a control unit in accordance with a program for controlling the blood pressure monitor 1 stored in the memory 51. For example, in the case where blood pressure measurement is executed via the oscillometric method, the CPU 100 drives the pump 32 (and the valve 33) in accordance with a blood pressure measurement start instruction from the operation portion 52 on the basis of a signal from the first pressure sensor 31. Also, the CPU 100 calculates the blood pressure value on the basis of a signal from the first pressure sensor 31, for example.

In the case where blood pressure measurement (estimation) based on pulse transit time is executed, the CPU 100 drives the valve 33 so that air inside the compression cuff 21 is discharged in accordance with a blood pressure measurement start instruction from the operation portion 52. Also, the CPU 100 drives the switching valve 35 and switches the connection destination of the pump 32 (and the valve 33) to the pressing cuff 24. Furthermore, the CPU 100 calculates the blood pressure value on the basis of a signal from the second pressure sensor 34.

The communication unit 59 is controlled by the CPU 100, sends predetermined information to an external device via a network 900 and receives information from an external device via the network 900, and relays the information to the CPU 100. The communication via the network 900 may be wireless or wired. In the present embodiment, the network 900 is the Internet (trademark), but it is not limited thereto. The network 900 may be another network such as an intra-hospital LAN or a one-to-one communication using a USB cable or the like. The communication unit 59 may include a USB connector.

The pump 32 and the valve 33 are connected to the compression cuff 21 and the pressing cuff 24 via the health device flow path formation member 600, the switching valve 35, and air lines 39a, 39b. Also, the first pressure sensor 31 is connected to the compression cuff 21 via an air line 38a.

The first pressure sensor 31 detects the pressure in the compression cuff 21. The second pressure sensor 34 is connected to the pressing cuff 24 via an air line 38b. The second pressure sensor 34 detects the pressure in the pressing cuff 24.

The switching valve 35 is driven in accordance with a control signal from the CPU 100 and switches the connection destination of the pump 32 and the valve 33 between the compression cuff 21 and the pressing cuff 24. The pump 32 includes a piezoelectric pump, for example. In the case where the connection destination of the pump 32 and the valve 33 is switched to the compression cuff 21 by the switching valve 35, the pump 32 supplies air, i.e., pressurization fluid, into the compression cuff 21 via the air line 39a. This pressurizes the inside of the compression cuff 21. In the case where the connection destination of the pump 32 and the valve 33 is switched to the pressing cuff 24 by the switching valve 35, the pump 32 supplies air, i.e., pressurization fluid, into the pressing cuff 24 via the air line 39b. This pressurizes the inside of the pressing cuff 24.

The pump 32 is provided with the valve 33, and the valve 33 is configured to be controlled to be opened and closed in accordance with the pump 32 being on and off.

When the connection destination of the pump 32 and the valve 33 is switched to the compression cuff 21 via the switching valve 35 and the pump 32 is turned on, the valve 33 closes. This allows air to be supplied inside the compression cuff 21. When the pump 32 is turned off, the valve 33 opens. This allows the air inside the compression cuff 21 to discharge out into the atmosphere via the air line 39a.

When the connection destination of the pump 32 and the valve 33 is switched to the pressing cuff 24 via the switching valve 35 and the pump 32 is turned on, the valve 33 closes. This allows air to be supplied inside the pressing cuff 24. When the pump 32 is turned off, the valve 33 opens. This allows the air inside the pressing cuff 24 to discharge out into the atmosphere via the air line 39b.

Note that, the valve 33 functions as a check valve, preventing the discharged air from flowing in reverse. The pump drive circuit 320 drives the pump 32 on the basis of a control signal from the CPU 100.

As the first pressure sensor 31, a piezoresistive pressure sensor can be used, for example. The first pressure sensor 31 is connected to the pump 32, the valve 33, and the compression cuff 21 via an air line 38a. The first pressure sensor 31 detects the pressure of the belt 20 (compression cuff 21) via the air line 38a and outputs a time series signal. Note that the pressure is detected using atmospheric pressure as a reference (zero).

The oscillation circuit 310 produces an oscillating electrical signal on the basis of the change in electric resistance of the first pressure sensor 31 due to the piezoresistive effect. In this way, the oscillation circuit 310 outputs to the CPU 100 a frequency signal having a frequency corresponding to the electrical signal value of the first pressure sensor 31. For example, the output of the first pressure sensor 31 is used to control the pressure of the compression cuff 21 and to calculate blood pressure values (including for systolic blood pressure and for diastolic blood pressure) via the oscillometric method.

In the case where blood pressure is measured in accordance with a typical oscillometric method, generally, the following occurs. Prior to measurement, the cuff is wrapped around the target measurement site (arm or the like) of the subject. In the measurement, the CPU 100 controls the pump 32 and the valve 33 to increase the cuff pressure above the systolic blood pressure, and then gradually decreases the cuff pressure. In the reducing pressure process, the cuff pressure is detected by the pressure sensor, and the variation of arterial volume generated in the artery at the target measurement site is determined to be a pulse wave signal. The systolic blood pressure and diastolic blood pressure are calculated on the basis of the change in amplitude of the pulse wave signal corresponding to the change in the cuff pressure at the time (mainly, a rising edge and a falling edge).

As the second pressure sensor 34, a piezoresistive pressure sensor can be used, for example. The second pressure sensor 34 is connected to the pump 32, the valve 33, and the pressing cuff 24 via an air line 38b. The second pressure sensor 34 detects the pressure of the pressing cuff 24 via the air line 38b and outputs a time series signal. Note that the pressure is detected using atmospheric pressure as a reference (zero).

The oscillation circuit 340 produces an oscillating electrical signal on the basis of the change in electric resistance in the second pressure sensor 34 due to the piezoresistive effect. In this way, the oscillation circuit 340 outputs to the CPU 100 a frequency signal having a frequency corresponding to the electrical signal value of the second pressure sensor 34. For example, the output of the second pressure sensor 34 is used to control the pressure of the pressing cuff 24 and to calculate the blood pressure on the basis of pulse transit time. When the pressure of the pressing cuff 24 is controlled to measure the blood pressure on the basis of pulse transit time, the CPU 100 controls the pump 32 and the valve 33 and increases and reduces the pressure, i.e., cuff pressure, in accordance with various conditions.

A battery 53 supplies power to the components disposed in the body 10 including, in the present embodiment, the CPU 100, the first pressure sensor 31, the pump 32, the valve 33, the display 50, the memory 51, the communication unit 59, the oscillation circuit 310, and the pump drive circuit 320. Also, the battery 53 supplies power to the current flow and voltage detection circuit 49 of the impedance measurement portion 40 via a wire 71. The wire 71 is disposed together with a wire 72 for signals between the band 23 and the compression cuff 21 of the belt 20 and extends in the circumferential direction of the belt 20 between the body 10 and the impedance measurement portion 40.

Figure 5A:
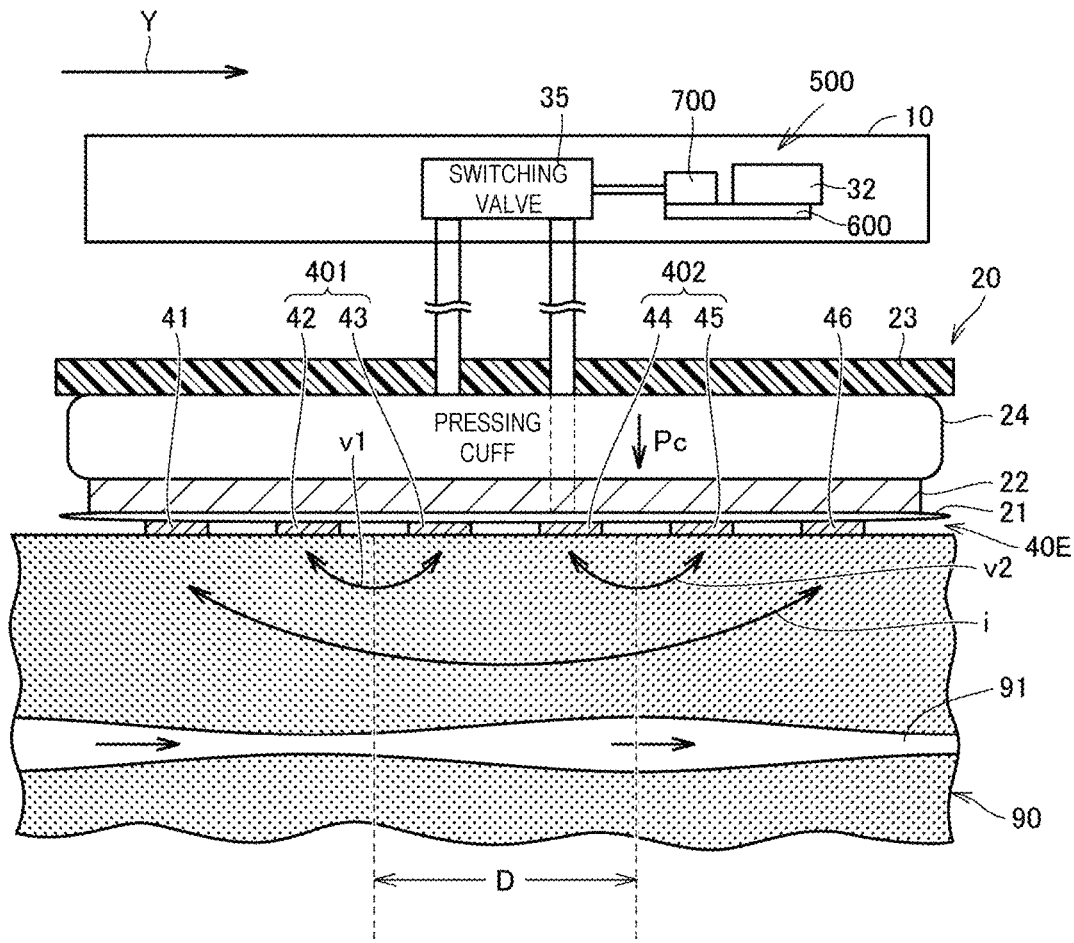
FIG. 5A is a diagram schematically illustrating the wrist blood pressure monitor according to the first embodiment in a cross section along the longitudinal direction of the wrist, the wrist blood pressure monitor being worn on the left wrist for blood pressure measurement based on pulse transit time.
Figure 5B:
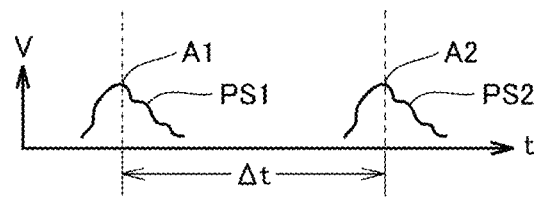
FIG. 5B is a diagram illustrating a first pulse wave signal waveform and a second pulse wave signal waveform output by the first pulse wave sensor and the second pulse wave sensor respectively in blood pressure measurement performed in the state illustrated in FIG. 5A.

FIG. 5A is a diagram schematically illustrating the wrist blood pressure monitor according to the first embodiment in a cross section along the longitudinal direction of the wrist, the wrist blood pressure monitor being worn on the left wrist for blood pressure measurement using pulse transit time. FIG. 5B is a diagram illustrating a first pulse wave signal waveform and a second pulse wave signal waveform output by the first pulse wave sensor and the second pulse wave sensor respectively in blood pressure measurement performed in the state illustrated in FIG. 5A.

The current flow and voltage detection circuit 49 of the impedance measurement portion 40 is controlled by the CPU 100. As illustrated in FIG. 5A, when the device is operating, the CPU 100 runs a high frequency constant current i between the current electrode pair 41, 46 disposed on either side in the longitudinal direction of the wrist (the width direction Y of the belt 20). For example, the high frequency constant current i is a current with a frequency of 50 kHz and a current value of 1 mA. With the high frequency constant current i running through the current electrode pair 41, 46, the current flow and voltage detection circuit 49 detects a voltage signal v1 between the first detection electrode pair 42, 43 of the first pulse wave sensor 401 and a voltage signal v2 between the second detection electrode pair 44, 45 of the second pulse wave sensor 402.

The voltage signals v1, v2 represent a change in electrical impedance caused by a pulse wave of the blood flow of the radial artery 91 at the portions corresponding to the where the first pulse wave sensor 401 and the second pulse wave sensor 402 are located on the palm side surface 90a of the left wrist 90 (impedance method). The current flow and voltage detection circuit 49 rectifies, amplifies, and filters the voltage signals v1, v2 and outputs a first pulse wave signal PS1 and a second pulse wave signal PS2 having a mountain-shaped waveform as illustrated in FIG. 5B as time series. In the present embodiment, the voltage signals v1, v2 are approximately 1 mV. Also, peaks A1, A2 of the first pulse wave signal PS1 and the second pulse wave signal PS2 are 1 V, for example.

Note that in the case where the pulse wave velocity (PWV) of the blood flow of the radial artery 91 ranges from 100 cm/s to 2000 cm/s, a time difference Δt between the first pulse wave signal PS1 and the second pulse wave signal PS2 ranges from 1.0 ms to 2.0 ms, where an actual interval D1 between the first pulse wave sensor 401 and the second pulse wave sensor 402 is 20 mm.

As illustrated in FIG. 5A, the pressing cuff 24 is in a pressurized state, and the compression cuff 21 is in a non-pressurized state with air being discharged from inside the compression cuff 21. The pressing cuff 24 is disposed, with respect to the artery direction of the radial artery 91, across the first pulse wave sensor 401, the second pulse wave sensor 402, and the current electrode pair 41, 46. Also, the solid material 22 is disposed, with respect to the artery direction of the radial artery 91, across the first pulse wave sensor 401, the second pulse wave sensor 402, and the current electrode pair 41, 46.

As such, when the pressing cuff 24 is pressurized by the pump 32, the first pulse wave sensor 401, the second pulse wave sensor 402, and the current electrode pair 41, 46 are pressed against the palm side surface 90a of the left wrist 90 by the solid material 22.

Note that the pressing force against the palm side surface 90a of the left wrist 90 of each of the current electrode pair 41, 46, the first pulse wave sensor 401, and the second pulse wave sensor 402 can be set appropriately.

In the present embodiment, the pressing cuff 24, which is a fluid bag, is used as the pressing portion. This allows the pump 32 and the valve 33 to be used together with the compression cuff 21 and allows the configuration to be simplified. Also, the first pulse wave sensor 401, the second pulse wave sensor 402, and the current electrode pair 41, 46 can be pressed by the solid material 22. This allows the pressing force against the target measurement site to be even. As a result, blood pressure measurement based on pulse transit time can be performed with high precision.

Figure 6:
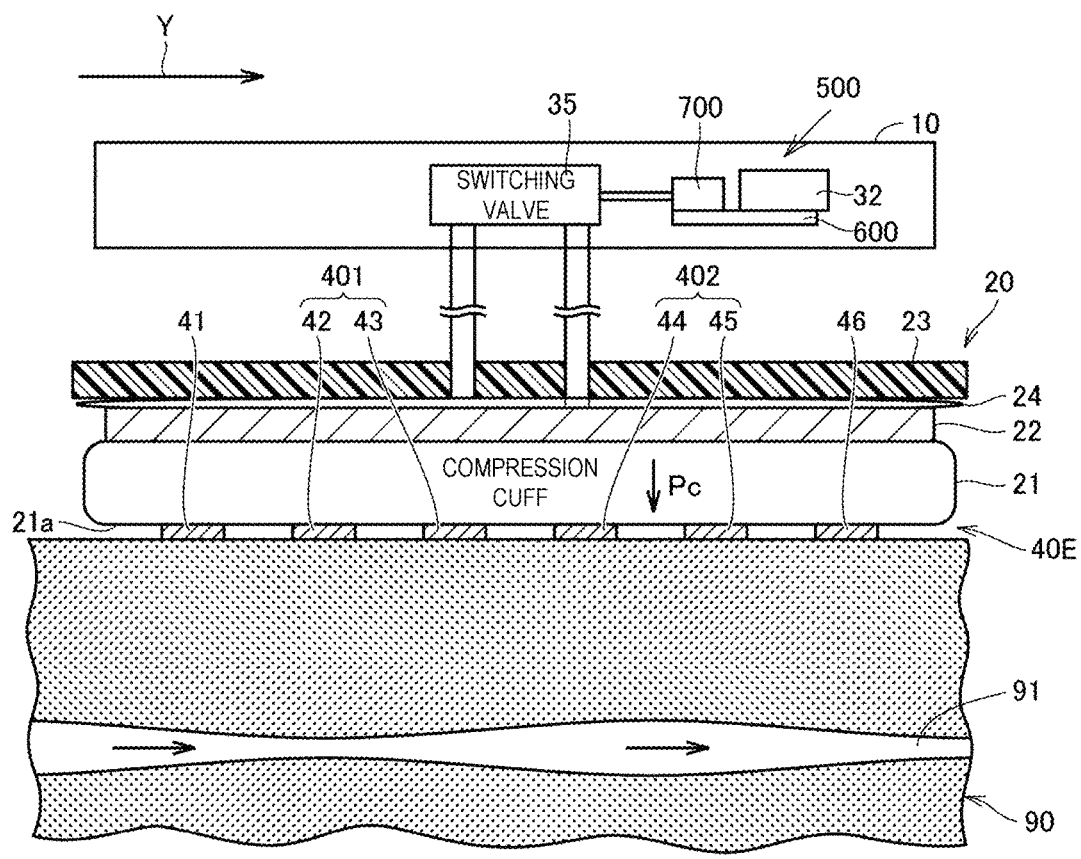
FIG. 6 is a diagram schematically illustrating the wrist blood pressure monitor according to the first embodiment in a cross section along the longitudinal direction of the wrist, the wrist blood pressure monitor being worn on the left wrist for blood pressure measurement via the oscillometric method.

FIG. 6 is a diagram schematically illustrating the wrist blood pressure monitor according to the first embodiment in a cross section along the longitudinal direction of the wrist, the wrist blood pressure monitor being worn on the left wrist for blood pressure measurement via the oscillometric method. In this case, the pressing cuff 24 is in a non-pressurized state with air being discharged from inside the pressing cuff 24, and the compression cuff 21 is in a state of being supplied with air. The compression cuff 21 extends in the circumferential direction of the left wrist 90 and compresses the left wrist 90 uniformly with respect to the circumferential direction of the left wrist 90 when pressurized by the pump 32. Between the inner circumferential surface of the compression cuff 21 and the left wrist 90, only the electrode group 40E is present. Thus, the blood vessel can be sufficiently closed without other members hindering the compression by the compression cuff 21. Thus, blood pressure measurement via the oscillometric method can be performed with high precision.

Figure 7:
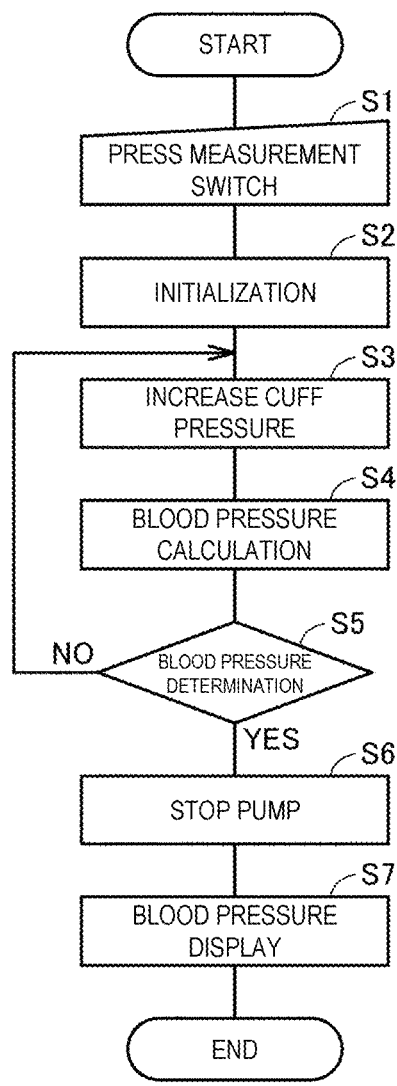
FIG. 7 is a diagram illustrating the operation flow of blood pressure measurement via the oscillometric method using the wrist blood pressure monitor according to the first embodiment.

FIG. 7 is a diagram illustrating the operation flow of blood pressure measurement via the oscillometric method using the wrist blood pressure monitor according to the first embodiment.

In the case where blood pressure measurement is performed via the oscillometric method, when the user sends an instruction for blood pressure measurement via the oscillometric method via the push type switch, i.e., the operation portion 52, provided on the body 10 (step S1), the CPU 100 starts operations and initializes a memory region for processing (step S2). The CPU 100 turns off the pump 32 via the pump drive circuit 320, opens the valve 33, and discharges the air in the compression cuff 21. Next, the output value of the first pressure sensor 31 at this time is set as a value corresponding to atmospheric pressure (adjusted to 0 mmHg).

Next, the CPU 100 closes the valve 33 and then drives the pump 32 via the pump drive circuit 320 to supply air to the compression cuff 21. This causes the compression cuff 21 to expand and the cuff pressure to gradually increase (step S3).

In the process of pressurizing, to calculate the blood pressure value, the CPU 100 monitors the cuff pressure via the first pressure sensor 31 and obtains, as a pulse wave signal, a variable component of the arterial volume generated in the radial artery 91 of the left wrist 90, i.e., the target measurement site.

Next, the CPU 100 functions as a second blood pressure calculation unit and attempts to calculate blood pressure values (of systolic blood pressure and diastolic blood pressure) on the basis of the obtained pulse wave signal at this point in time via the oscillometric method using a known algorithm.

At this point, if the blood pressure value cannot be calculated due to a lack of data (step S5: NO), unless the cuff pressure reaches an upper pressure limit, the processing of steps S3 to S5 are repeated. Note that the upper pressure limit is set in advance and may be 300 mmHg, for example.

If the blood pressure values can be calculated (step S5: YES), the CPU 100 stops the pump 32 via the pump drive circuit 320, opens the valve 33, and discharges the air in the compression cuff 21 (step S6). Lastly, the CPU 100 displays the blood pressure value measurement results on the display 50 and stores them in the memory 51 (step S7).

Note that the calculation of the blood pressure values is not limited being performed in the pressurizing process as described above and may be performed in the depressurizing process.

Figure 8:
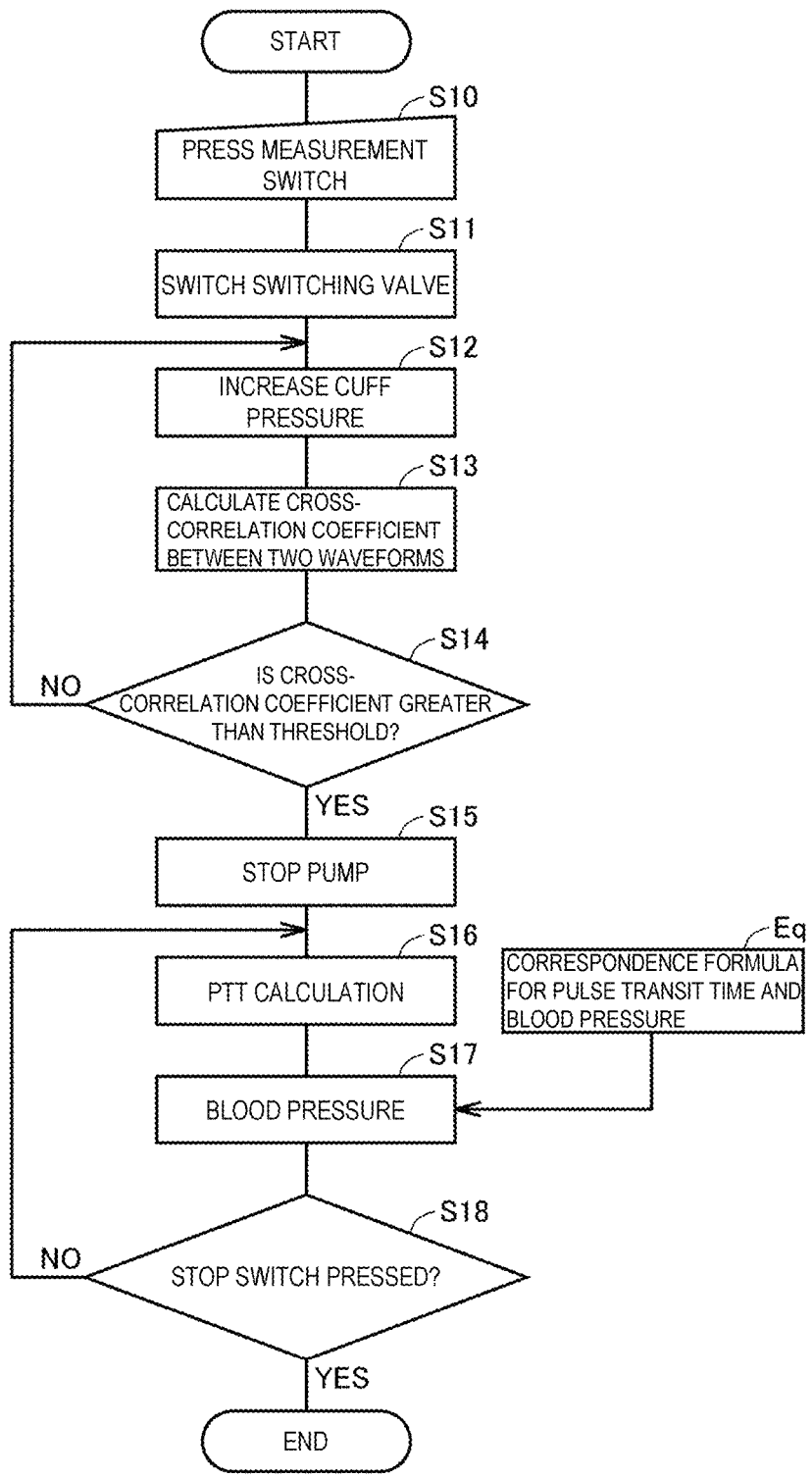
FIG. 8 is a diagram illustrating the operation flow of blood pressure measurement (estimation) based on pulse transit time (PTT) using the wrist blood pressure monitor according to the first embodiment to obtain pulse transit time.

FIG. 8 is a diagram illustrating the operation flow of blood pressure measurement (estimation) based on pulse transit time (PTT) using the wrist blood pressure monitor according to the first embodiment to obtain pulse transit time.

As illustrated in FIG. 8, in the case where blood pressure measurement (estimation) is performed on the basis of pulse transit time, when the user sends an instruction for blood pressure measurement based on PTT via the push type switch, i.e., the operation portion 52, provided on the body 10 (step S10), the CPU 100 drives the switching valve 35 and switches the connection destination of the pump 32 and the valve 33 to the pressing cuff 24 (step S11). Next, the CPU 100 closes the valve 33 and drives the pump 32 via the pump drive circuit 320 to supply air to the pressing cuff 24. This causes the pressing cuff 24 to expand and the cuff pressure to gradually increase (step S12). For example, the cuff pressure is continuously increased at a constant speed by 5 mmHg/s. Note that the cuff pressure may be increased in steps to secure enough time to calculate a cross-correlation coefficient r described below.

In the pressurizing process, the CPU 100 functions a cross-correlation coefficient calculation unit, obtains the first pulse wave signal PS1 and the second pulse wave signal PS2 output as time series by the first pulse wave sensor 401 and the second pulse wave sensor 402, and calculates in real time the cross-correlation coefficient r between the waveforms of the first pulse wave signal PS1 and the second pulse wave signal PS2 (step S13).

Also, the CPU 100 functions as a pressing force setting unit and determines whether the calculated cross-correlation coefficient r is greater than a preset threshold Th (step S14). For example, the threshold Th is 0.99.

If the cross-correlation coefficient r is equal to or less than the threshold Th (step S14: NO), the processing of steps S12 to S14 is repeated until the cross-correlation coefficient r is greater than the threshold Th. If the cross-correlation coefficient r is greater than the threshold Th (step S14: YES), the CPU 100 stops the pump 32 (step S15) and sets the cuff pressure as the current value, i.e., the value at the point in time when the cross-correlation coefficient r became greater than the threshold Th.

In this state, the CPU 100 obtains the time difference $\Delta t$ (see FIG. 5B) between the first pulse wave signal PS1 and the second pulse wave signal PS2 as a pulse transit time PTT (step S16). Specifically, the time difference $\Delta t$ between the peak A1 of the first pulse wave signal PS1 and the peak A2 of the second pulse wave signal PS2 in FIG. 5B is determined to be the pulse transit time.

Obtaining the pulse transit time in this way can increase the measurement precision of the pulse transit time. Also, by setting the cuff pressure as the value at the point in time when the cross-correlation coefficient r became greater than the threshold Th, the pulse transit time can be obtained without needlessly increasing cuff pressure. This can reduce the physical burden on the user.

Next, the CPU 100 functions as a first blood pressure calculation unit and calculates (estimates) blood pressure on the basis of the pulse transit time obtained in step S16 using a preset correspondence formula for pulse transit time and blood pressure (step S17).

By blood pressure being calculated (estimated) in this way, the measurement precision of pulse transit time described above can be increased and blood pressure measurement precision can be increased. Note that the blood pressure value measurement results are displayed on the display 50 and stored in the memory 51.

In the present embodiment, in step S18, if a measurement stop instruction has not been received via the operation portion 52 (step S18: NO), calculation of pulse transit time (step S16) and calculation of blood pressure (step S17) are periodically repeated every time the first pulse wave signal PS1 and the second pulse wave signal PS2 corresponding to the pulse wave are input. The CPU 100 updates and displays the blood pressure value measurement results on the display 50 and cumulatively stores them in the memory 51. Then, if a measurement stop instruction has been received in step S18 (step S18: YES), measurement operation ends.

According to the blood pressure monitor 1, blood pressure can be continuously measured over an extended period of time on the basis of pulse transit time while keeping the physical burden on the user light.

Also, according to the blood pressure monitor 1, blood pressure measurement (estimation) based on pulse transit time and blood pressure measurement via the oscillometric method can be performed by one device. This can increase user convenience.

Figure 9:
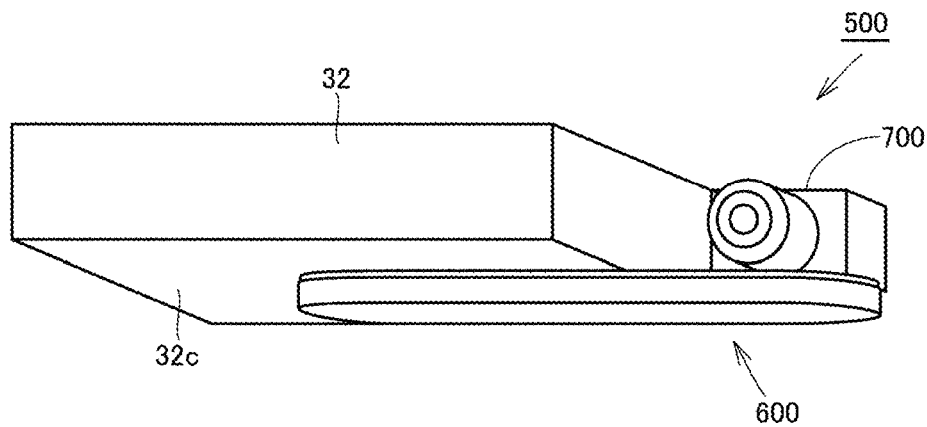
FIG. 9 is a perspective view illustrating a health device flow path formation unit according to a first embodiment.
Figure 10:
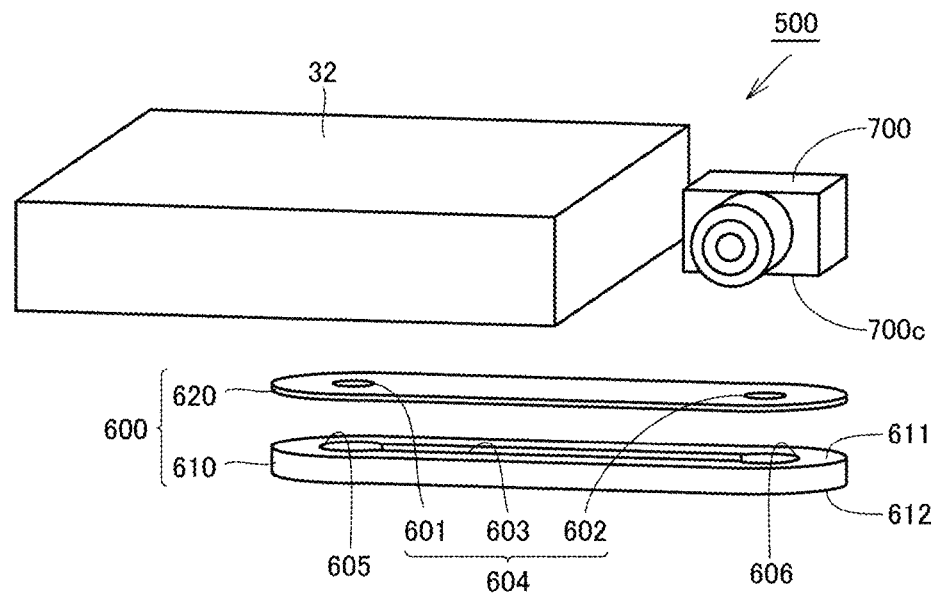
FIG. 10 is an exploded perspective view illustrating the health device flow path formation unit according to the first embodiment.
Figure 11:
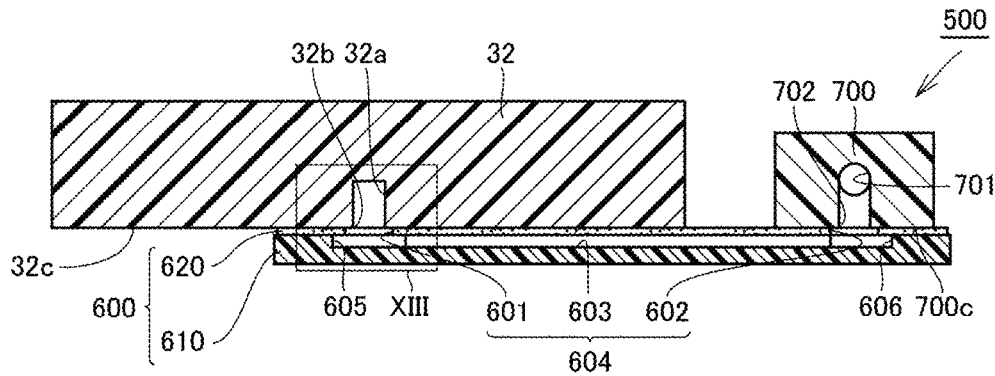
FIG. 11 is a cross-sectional view illustrating the health device flow path formation unit according to the first embodiment.

FIG. 9 is a perspective view illustrating the health device flow path formation unit according to a first embodiment. FIG. 10 is an exploded perspective view illustrating the health device flow path formation unit according to the first embodiment. FIG. 11 is a cross-sectional view illustrating the health device flow path formation unit according to the first embodiment. The health device flow path formation unit 500 according to the first embodiment will be described with reference to FIGS. 9 to 11.

As illustrated in FIGS. 9 to 11, the health device flow path formation unit 500 according to the first embodiment includes the pump 32, i.e., a first target attachment member, the connection member 700, i.e., a second target attachment member, and the health device flow path formation member 600.

The pump 32 includes a lower surface 32c, i.e., a first target attachment surface, where a first end of the health device flow path formation member 600 is attached. The lower surface 32c of the pump 32 has, for example, a planar shape. The pump 32 internally includes a fluid path 32a along which a fluid flows. A supply opening 32b of the fluid path 32a is provided on the lower surface 32c. The inner diameter of the supply opening 32b is less than the inner diameter of a first opening portion 601 of the health device flow path formation member 600 described below.

The connection member 700 includes a lower surface 700c, i.e., a second target attachment surface, where a second end of the health device flow path formation member 600 is attached. The connection member 700 internally includes a fluid path 701 along which a fluid flows. An inlet 702 of the fluid path 701 is provided on the lower surface 700c. The inner diameter of the inlet 702 is less than the inner diameter of a second opening portion 602 of the health device flow path formation member 600 described below.

The health device flow path formation member 600 includes a flow path 604 for supplying air, i.e., fluid, to the compression cuff 21 or the pressing cuff 24, i.e., a target supply member. The health device flow path formation member 600 includes the first opening portion 601, the second opening portion 602, and a connection path 603. The first opening portion 601, the second opening portion 602, and the connection path 603 constitute the flow path 64.

The first opening portion 601 is located at the first end of the flow path 604. The second opening portion 602 is located at the second end of the flow path 604. The connection path 603 connects together the first opening portion 601 and the second opening portion 602.

The health device flow path formation member 600 includes a plate-like member 610 and a joining layer 620. The plate-like member 610 has a flat shape. The plate-like member 610 includes a first main surface 611 and a second main surface 612 that are the front and back surfaces in the thickness direction (a first direction described below). The plate-like member 610 is formed by injection molding, for example. The plate-like member 610 is made of a resin member, metal member, or the like.

The plate-like member 610 includes the connection path 603. The connection path 603 has an opening shape that opens to the first main surface 611. A first chamber 605 is formed at the first end of the connection path 603, and a second chamber 606 is formed at the second end of the connection path 603. The first chamber 605 and the second chamber 606 have a substantially cylindrical shape and have a greater width than that of the portion of the connection path 603 connecting the first chamber 605 and the second chamber 606. Note that the first chamber 605 and the second chamber 606 may have the same width as that of the portion of the connection path 603 connecting the first chamber 605 and the second chamber 606.

The joining layer 620 has an elongated shape. The joining layer 620 is made of double-sided tape, an adhesive, or the like, for example. The joining layer 620 is disposed such that the pump 32 overlaps with the first end of the joining layer 620, and the second end of the joining layer 620 protrudes from the pump 32. The joining layer 620 is provided with the first opening portion 601 and the second opening portion 602.

The joining layer 620 joins the first end of the plate-like member 610 to the lower surface 32c (the first target attachment surface) of the pump 32 so that the first opening portion 601 communicates with the fluid path 32a of the pump 32. The joining layer 620 joins the second end of the plate-like member 610 to the lower surface 700c (the second target attachment surface) of the connection member 700 so that the second opening portion 602 communicates with the fluid path 701 of the connection member 700.

Figure 12:
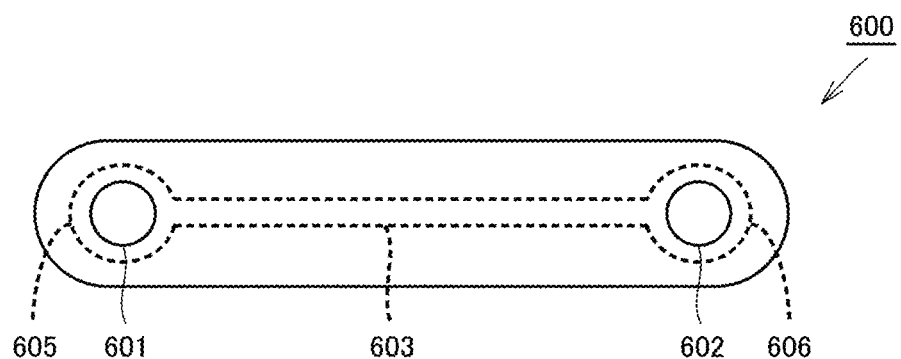
FIG. 12 is a top view illustrating the health device flow path formation member according to the first embodiment.
Figure 13:
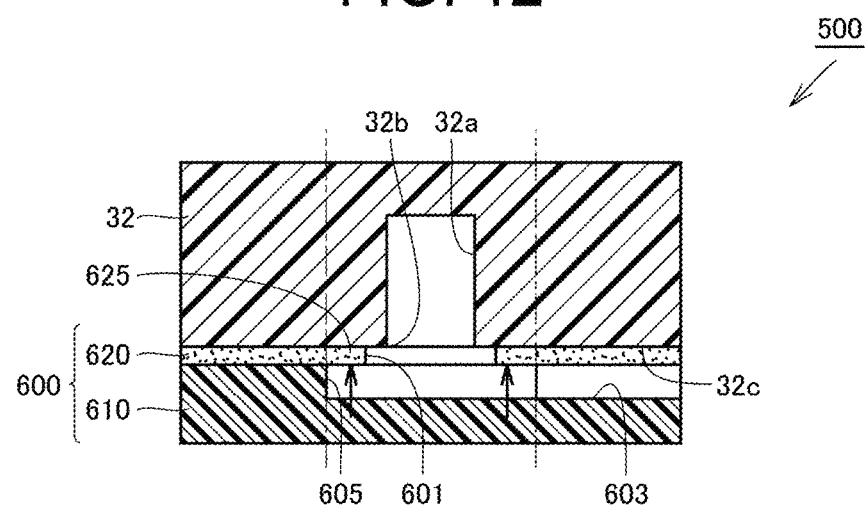
FIG. 13 is a cross-sectional view illustrating a first opening portion side of the health device flow path formation unit according to the first embodiment. This is an enlarged view of a portion enclosed by line XIII illustrated in FIG. 11.
Figure 14:
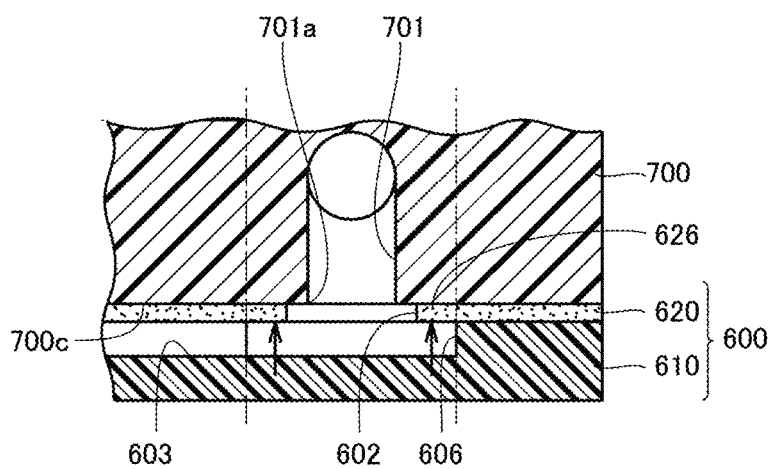
FIG. 14 is a cross-sectional view illustrating a second opening portion side of the health device flow path formation unit according to the first embodiment.

FIG. 12 is a top view illustrating the health device flow path formation member according to a first embodiment. FIG. 13 is a cross-sectional view illustrating the first opening portion side of the health device flow path formation unit according to the first embodiment. This is an enlarged view of a portion enclosed by line XIII illustrated in FIG. 11. FIG. 14 is a cross-sectional view illustrating the second opening portion side of the health device flow path formation unit according to the first embodiment. The positional relationship between the first opening portion 601 and the second opening portion 602 and the connection path 603 will be described with reference to FIGS. 12 to 14.

As illustrated in FIGS. 12 and 13, when viewed in the first direction in which the joining layer 620 and the plate-like member 610 overlap, the first opening portion 601 is disposed inward a distance from a profile line (the dotted line portion of FIG. 12) of the projection of the connection path 603 in the first direction, forming a first protrusion portion 625 (see FIG. 13) in the joining layer 620 that protrudes inward from the profile line.

In the case where the health device flow path formation member 600 is attached to the lower surface 32c of the pump 32, the first protrusion portion 625 is attached to the lower surface 32c and is disposed around the supply opening 32b of the pump 32.

Thus, when air is supplied from the pump 32 to the target supply member via the health device flow path formation member 600, a portion of the air supplied from the supply opening 32b of the pump 32 to inside the connection path 603 bounces of the bottom surface portion of the connection path 603, making the first protrusion portion 625 press against the lower surface 32c of the pump 32.

As a result, the adhesion between the joining layer 620 and the lower surface 32c of the pump 32 is increased. Also, by the first protrusion portion 625 pressing against the lower surface 32c, air can be prevented from entering the interface between the joining layer 620 and the lower surface 32c of the pump 32. As a result, good air tightness is maintained between health device flow path formation member 600 and the pump 32.

As illustrated in FIGS. 12 to 14, when viewed in the first direction, the second opening portion 602 is disposed inward a distance from a profile line of the projection of the connection path 603 in the first direction, forming a second protrusion portion 626 in the joining layer 620 that protrudes inward from the profile line.

In the case where the health device flow path formation member 600 is attached to the lower surface 700c of the connection member 700, the second protrusion portion 626 is attached to the lower surface 700c and is disposed around the inlet 702 of the connection member 700.

Thus, when air is supplied from the pump 32 to the target supply member via the health device flow path formation member 600, a portion of the air discharged from the connection path 603 toward an inlet 701a presses the second protrusion portion 626 against the lower surface 700c of the connection member 700. As a result, the adhesion between the joining layer 620 and the lower surface 700c of the connection member 700 is increased. Also, by the second protrusion portion 626 pressing against the lower surface 700c, air can be prevented from entering the interface between the joining layer 620 and the lower surface 700c of the connection member 700. As a result, good air tightness is maintained between the health device flow path formation member 600 and the connection member 700.

Also, the health device flow path formation member 600 is configured to join to a first target placement surface (the lower surface 32c) of the pump 32. Thus, the supply opening 32b is provided on the first target placement surface of the pump 32, and the health device flow path formation member 600 is directly joined to the first target placement surface so that the flow path 604 of the health device flow path formation member 600 communicates with the supply opening 32b. This allows the height (size) of the health device flow path formation unit 500 and the blood pressure monitor 1 provided with the same to be decreased.

In a similar manner, the health device flow path formation member 600 is configured to join to a second target placement surface (the lower surface 700c) of the connection member 700. Thus, the inlet 702 is provided on the second target placement surface of the connection member 700, and the health device flow path formation member 600 is directly joined to the second target placement surface so that the flow path 604 of the health device flow path formation member 600 communicates with the inlet 702. This allows the height (size) of the health device flow path formation unit 500 and the blood pressure monitor 1 provided with the same to be decreased.

Modified Example 1

Figure 15:
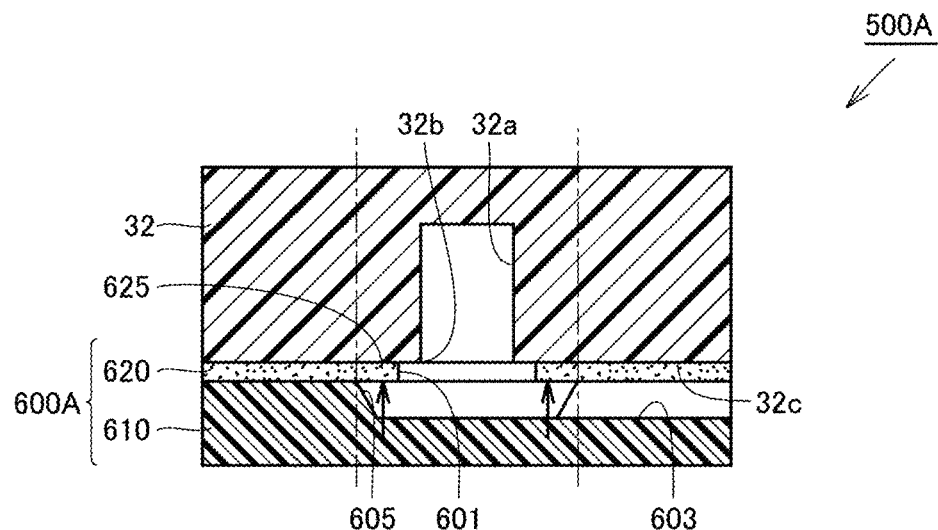
FIG. 15 is a cross-sectional view illustrating a first opening portion side of a health device flow path formation unit according to a first modified example.

FIG. 15 is a cross-sectional view illustrating the first opening portion side of a health device flow path formation unit according to a first modified example. A health device flow path formation unit 500A will be described with reference to FIG. 15.

As illustrated in FIG. 15, the health device flow path formation unit 500A according to the first modified example is different from the health device flow path formation unit 500 according to the first embodiment in that the connection path 603 of a health device flow path formation member 600A has a different shape. Other configurations are substantially similar.

In the first modified example, a portion of the connection path 603 located at the first end includes a tapered portion that tapers becoming thinner in the first direction in the direction away from the joining layer 620. Specifically, a portion of the inner surface of the plate-like member 610 that defines the first chamber 605 tapers at an incline becoming thinner in the first direction in the direction away from the joining layer 620.

Also, a portion of the connection path 603 located at the second end includes a tapered portion that tapers becoming thinner in the first direction in the direction away from the joining layer 620. Specifically, a portion of the inner surface of the plate-like member 610 that defines the second chamber 606 tapers at an incline becoming thinner in the first direction in the direction away from the joining layer 620.

With such a configuration, the health device flow path formation member 600A according to the first modified example can obtain effects similar to that of the health device flow path formation member 600 according to the first embodiment. Also, the health device flow path formation unit 500A and the health device according to the first modified example that include the health device flow path formation member 600A can obtain effects similar to that of the health device flow path formation unit 500 and the blood pressure monitor 1 according to the first embodiment.

Also, because of the portions located at either end of the connection path 603 including a tapered portion, the joining strength of the joining layer 620 for the pump 32 and the connection member 700 can be maintained and the area of the first protrusion portion 625 and the second protrusion portion 626 can be increased. Accordingly, the air tightness between the health device flow path formation member 600A and the pump 32 and the air tightness between the health device flow path formation member 600A and the connection member 700 can be better maintained.

Comparative Example

Figure 16:
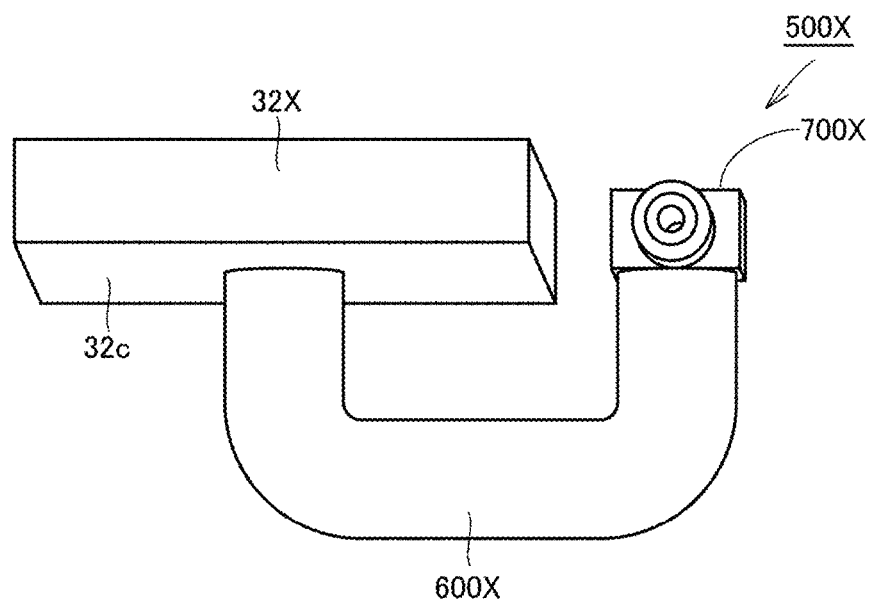
FIG. 16 is a perspective view illustrating a health device flow path formation unit according to a comparative example.
Figure 17:
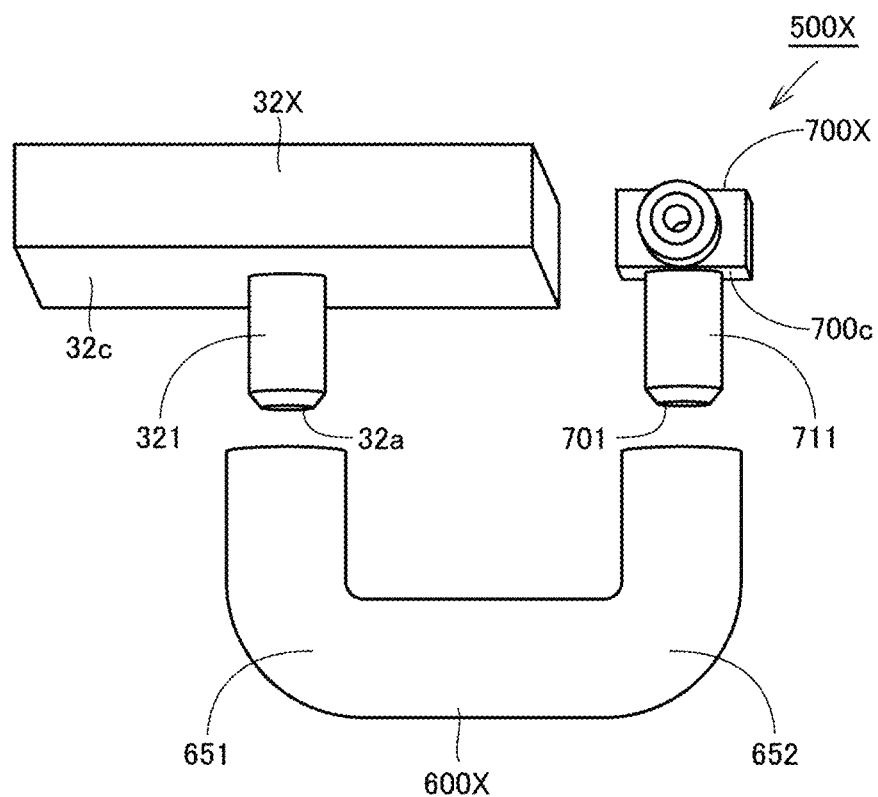
FIG. 17 is an exploded perspective view illustrating the health device flow path formation unit according to a comparative example.

FIG. 16 is a perspective view illustrating the health device flow path formation unit according to a comparative example. FIG. 17 is an exploded perspective view illustrating the health device flow path formation unit according to the comparative example. A health device flow path formation unit 500X will be described with reference to FIGS. 16 and 17.

As illustrated in FIGS. 16 and 17, the health device flow path formation unit 500X according to the comparative example is different from the health device flow path formation unit 500 according to the first embodiment in that a pump 32X, a connection member 700X, and a health device flow path formation member 600X have different configurations.

The pump 32X includes a nozzle 321 including the fluid path 32a. The nozzle 321 projects downward from the lower surface 32c of the pump 32X. The connection member 700X includes a nozzle 711 including the fluid path 701. The nozzle 711 projects downward from the lower surface 700c of the connection member 700X.

The health device flow path formation member 600X includes a tube with flexibility. The first end of the health device flow path formation member 600X is engaged with the nozzle 321. The second end of the health device flow path formation member 600X is engaged with the nozzle 711. In this state, the health device flow path formation member 600X is formed with a bend flow path including bend portions 651, 652.

Thus, the health device flow path formation unit 500X including the pump 32X, the connection member 700X, and the health device flow path formation member 600X is formed relatively thick to conform to the thickness of the bend portion 651 or the bend portion 652 and the nozzle 321 or the nozzle 711. As a result, the health device flow path formation unit 500X and a blood pressure monitor including the same are difficult to decrease in size.

Note that in the case where the pump 32X and the connection member 700X are connected using the health device flow path formation member 600 according to the first embodiment, because the bend portions 651, 652 are not formed, the height of the health device flow path formation unit and the blood pressure monitor can be decreased by an amount corresponding to the thickness of the bend portions 651, 652.

Second Embodiment

Figure 18:
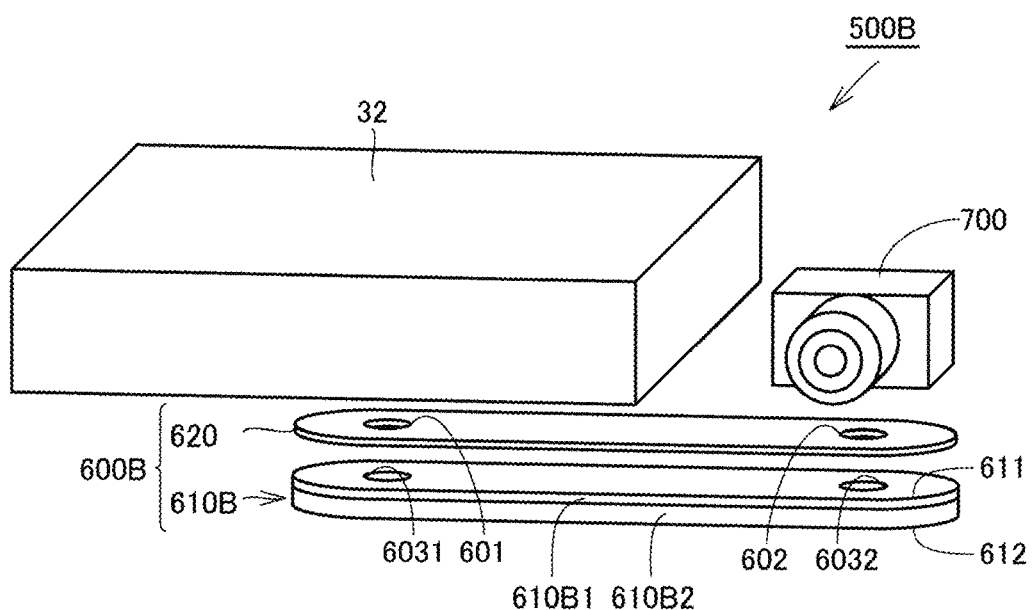
FIG. 18 is an exploded perspective view illustrating a health device flow path formation unit according to a second embodiment.
Figure 19:
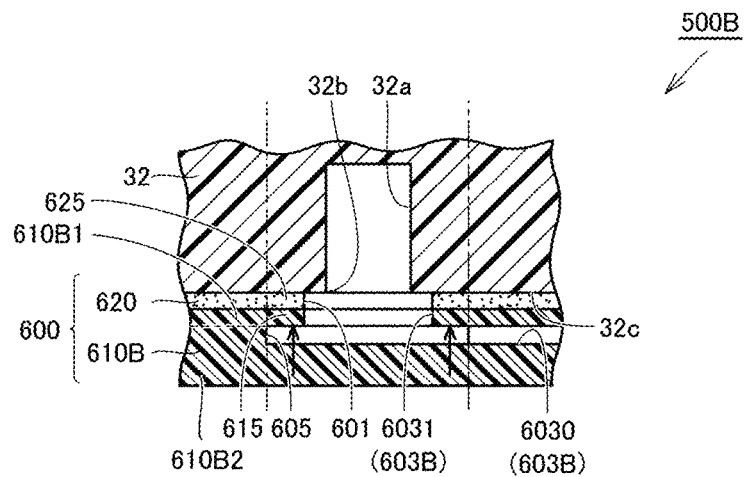
FIG. 19 is a cross-sectional view illustrating a first opening portion side of the health device flow path formation unit according to the second embodiment.
Figure 20:
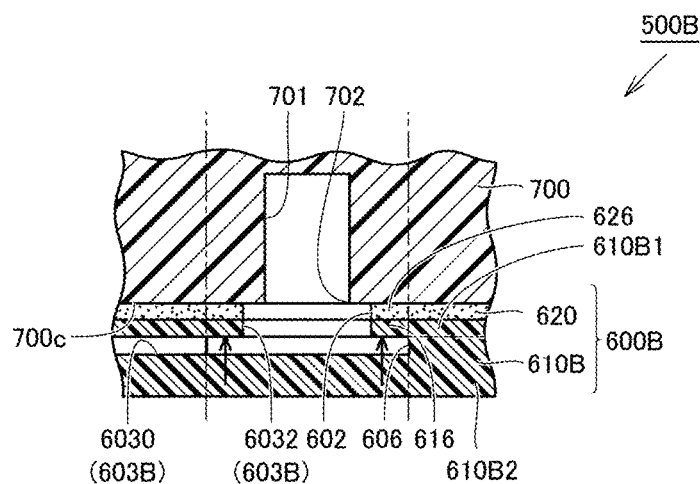
FIG. 20 is a cross-sectional view illustrating a second opening portion side of the health device flow path formation unit according to the second embodiment.

FIG. 18 is an exploded perspective view illustrating a health device flow path formation unit according to a second embodiment. FIG. 19 is a cross-sectional view illustrating the first opening portion side of the health device flow path formation unit according to the second embodiment. FIG. 20 is a cross-sectional view illustrating the second opening portion side of the health device flow path formation unit according to the second embodiment. A health device flow path formation unit 500B according to the second embodiment will be described with reference to FIGS. 18 to 20.

As illustrated in FIGS. 18 to 20, the health device flow path formation unit 500B according to the second embodiment is different from the health device flow path formation unit 500 according to the first embodiment in that a connection path 603B and a plate-like member 610B of a health device flow path formation member 600B have different configurations. Other configurations are substantially similar.

The plate-like member 610B includes a first portion 610B1 and a second portion 610B2. The first portion 610B1 has a plate-like shape. The first portion 610B1 is located on one side of the plate-like member 610B in the thickness direction (the first direction). The first portion 610B1 includes two through holes, a first auxiliary path portion 6031 and a second auxiliary path portion 6032 described below.

The second portion 610B2 has a plate-like shape. The second portion 610B2 is located on the other side in the thickness direction. The second portion 610B2 includes a groove portion that opens toward the first portion 610B1 in the thickness direction. The groove defines a main path portion 6030 described below.

The first portion 610B1 is disposed and fixed above the second portion 610B2 covering the groove portion to form the plate-like member 610B.

Note that the position in the thickness direction where the first portion 610B1 and the second portion 610B2 are divided is not limited to the position described above and can be any appropriate position. The plate-like member 610B may be formed by disposing and fixing the first portion 610B1 above the second portion 610B2 with the groove portion of the first portion 610B1 and a groove portion of the second portion 610B2 being disposed opposing one another.

The connection path 603B includes the main path portion 6030 provided inside the plate-like member 610B, the first auxiliary path portion 6031, and the second auxiliary path portion 6032.

The main path portion 6030 is provided inside the plate-like member 610B. The first chamber 605 is provided on the first end of the main path portion 6030. The second chamber 606 is provided on the second end of the main path portion 6030.

As illustrated in FIG. 19, the first auxiliary path portion 6031 connects the first opening portion 601 and the main path portion 6030. When viewed in the first direction in which the joining layer 620 and the plate-like member 610B overlap, the first auxiliary path portion 6031 is disposed inward from the main path portion 6030, forming a first projection portion 615 in the plate-like member 610B that defines the first auxiliary path portion 6031 and projects inward from the main path portion 6030. The first auxiliary path portion 6031 is located inward from the first chamber 605 when viewed in the first direction. The first protrusion portion 625 is supported by the first projection portion 615.

When air is supplied from the pump 32 to the target supply member via the health device flow path formation member 600B, a portion of the air supplied from the supply opening 32b of the pump 32 to inside the connection path 603B bounces of the bottom surface portion of the connection path 603B, and the air from the bottom surface portion presses the first projection portion 615 toward the lower surface 32c of the pump 32. Thus, the first projection portion 615 presses the first protrusion portion 625 against the lower surface 32c of the pump 32.

As a result, the adhesion between the joining layer 620 and the lower surface 32c of the pump 32 is increased. Also, by the first protrusion portion 625 pressing against the lower surface 32c, air can be prevented from entering the interface between the joining layer 620 and the lower surface 32c of the pump 32. As a result, good air tightness is maintained between the health device flow path formation member 600B and the pump 32.

As illustrated in FIG. 20, the second auxiliary path portion 6032 connects the second opening portion 602 and the main path portion 6030. When viewed in the first direction, the second auxiliary path portion 6032 is disposed inward from the main path portion 6030, forming a second projection portion 616 in the plate-like member 610B that defines the second auxiliary path portion 6032 and projects inward from the main path portion 6030. The second auxiliary path portion 6032 is located inward from the second chamber 606 when viewed in the first direction. The second protrusion portion 626 is supported by the second projection portion 616.

When air is supplied from the pump 32 to the target supply member via the health device flow path formation member 600B, a portion of the air discharged from the connection path 603 toward an inlet 701a presses the second projection portion 616 toward the lower surface 700c of the connection member 700. As a result, the second projection portion 616 presses the second protrusion portion 626 against the lower surface 700c of the connection member 700.

As a result, the adhesion between the joining layer 620 and the lower surface 700c of the connection member 700 is increased. Also, by the second protrusion portion 626 pressing against the lower surface 700c, air can be prevented from entering the interface between the joining layer 620 and the lower surface 700c of the connection member 700. As a result, good air tightness is maintained between the health device flow path formation member 600B and the connection member 700.

With such a configuration, the health device flow path formation member 600B according to the second embodiment can obtain effects similar to that of the health device flow path formation member 600 according to the first embodiment. Also, the health device flow path formation unit 500B and the blood pressure monitor according to the second embodiment that include the health device flow path formation member 600B can obtain effects similar to that of the health device flow path formation unit 500 and the blood pressure monitor 1 according to the first embodiment.

Third Embodiment

Figure 21:
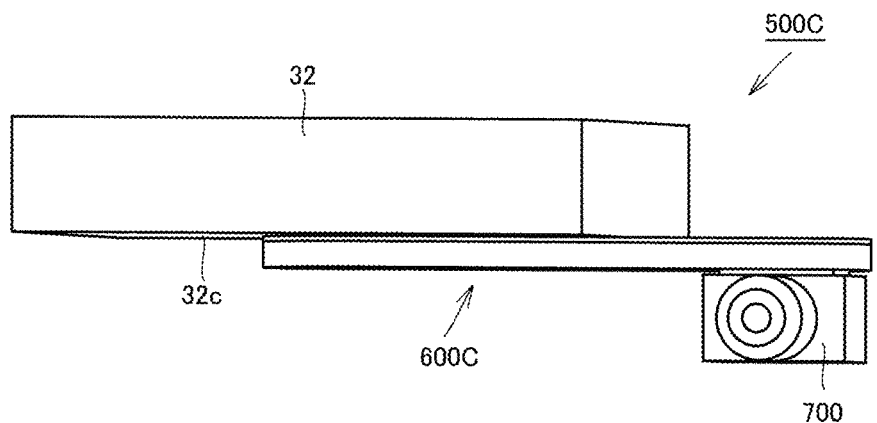
FIG. 21 is a perspective view illustrating a health device flow path formation unit according to a third embodiment.
Figure 22:
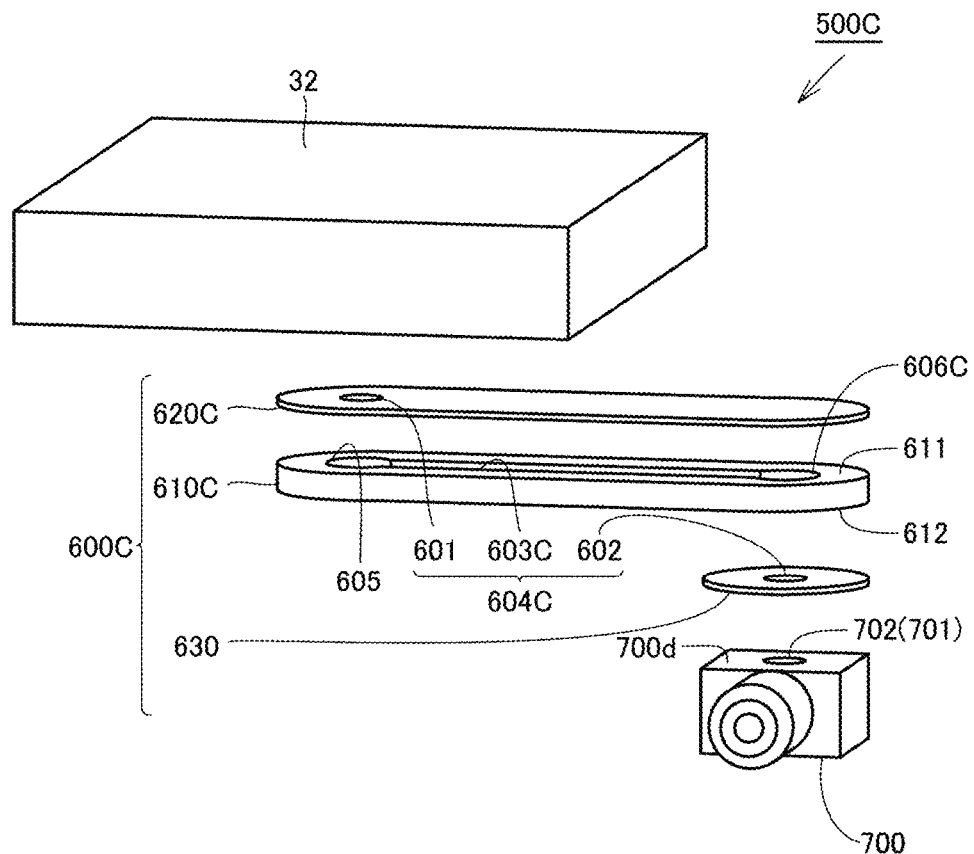
FIG. 22 is an exploded perspective view illustrating the health device flow path formation unit according to the third embodiment.
Figure 23:
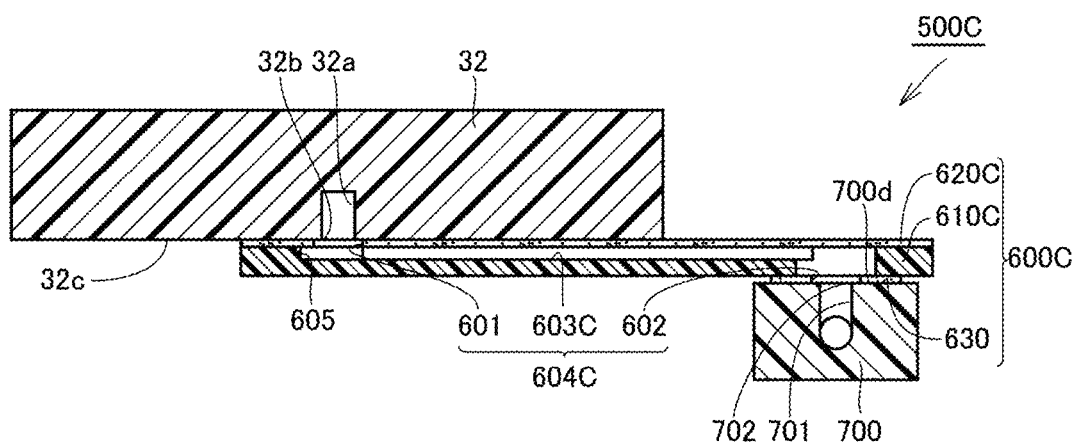
FIG. 23 is a cross-sectional view illustrating the health device flow path formation unit according to the third embodiment.

FIG. 21 is a perspective view illustrating a health device flow path formation unit according to a third embodiment. FIG. 22 is an exploded perspective view illustrating the health device flow path formation unit according to the third embodiment. FIG. 23 is a cross-sectional view illustrating the health device flow path formation unit according to the third embodiment. A health device flow path formation unit 500C according to the third embodiment will be described with reference to FIGS. 21 to 23.

As illustrated in FIGS. 21 to 23, the health device flow path formation unit 500C according to the third embodiment is different from the health device flow path formation unit 500 according to the first embodiment in that the attachment position of the connection member 700 and the configuration of a health device flow path formation member 600C are different. Other configurations are substantially similar.

The connection member 700 is attached to the second main surface 612 of a plate-like member 610C. The connection member 700 includes an upper surface 700d, i.e., a second target attachment surface, where a second end of the health device flow path formation member 600C is attached. The connection member 700 internally includes a fluid path 701 along which a fluid flows. An inlet 702 of the fluid path 701 is provided on the upper surface 700d.

The health device flow path formation member 600C includes the plate-like member 610C, a joining layer 620C, and a connection layer 630.

The plate-like member 610C is different from the plate-like member 610 according to the first embodiment in that the second end opens to the second main surface 612. Other configurations are substantially similar. A second chamber 606C of the plate-like member 610C opens to the first main surface 611 and the second main surface 612.

The joining layer 620C is provided with the first opening portion 601. The joining layer 620C is disposed on the first main surface 611 covering the connection path 603C except at a portion where the first opening portion 601 overlaps with the connection path 603C in the first direction. The joining layer 620C joins the first end of the plate-like member 610C to the lower surface 32c of the pump 32 so that the first opening portion 601 communicates with the fluid path 32a of the pump 32.

The connection layer 630 has a substantially circular shape. The connection layer 630 is made of double-sided tape, an adhesive, or the like, for example. The connection layer 630 is provided with the second opening portion 602. The connection layer 630 is disposed on the second main surface 612. The connection layer 630 joins the second end of the plate-like member 610C to the upper surface 700d of the connection member 700 so that the second opening portion 602 communicates with the fluid path 701 of the connection member 700.

When viewed in the first direction, the second opening portion 602 is disposed inward a distance from a profile line of the projection of the connection path 603C in the first direction, forming a second protrusion portion 636 in the connection layer 630 that protrudes inward from the profile line.

When air is supplied from the pump 32 to the target supply member via the health device flow path formation member 600C, a portion of the air discharged from the connection path 603C toward an inlet 701a presses the second protrusion portion 636 against the upper surface 700d of the connection member 700. As a result, the adhesion between the connection layer 630 and the upper surface 700d of the connection member 700 is increased. Also, by the second protrusion portion 636 pressing against the upper surface 700d, air can be prevented from entering the interface between the connecting layer 630 and the upper surface 700d of the connection member 700. As a result, good air tightness is maintained between the health device flow path formation member 600C and the connection member 700.

With such a configuration, the health device flow path formation member 600C according to the third embodiment can obtain effects similar to that of the health device flow path formation member 600 according to the first embodiment. Also, the health device flow path formation unit 500C and the blood pressure monitor according to the third embodiment that include the health device flow path formation member 600C can obtain effects similar to that of the health device flow path formation unit 500 and the blood pressure monitor 1 according to the first embodiment.

Fourth Embodiment

Figure 24:
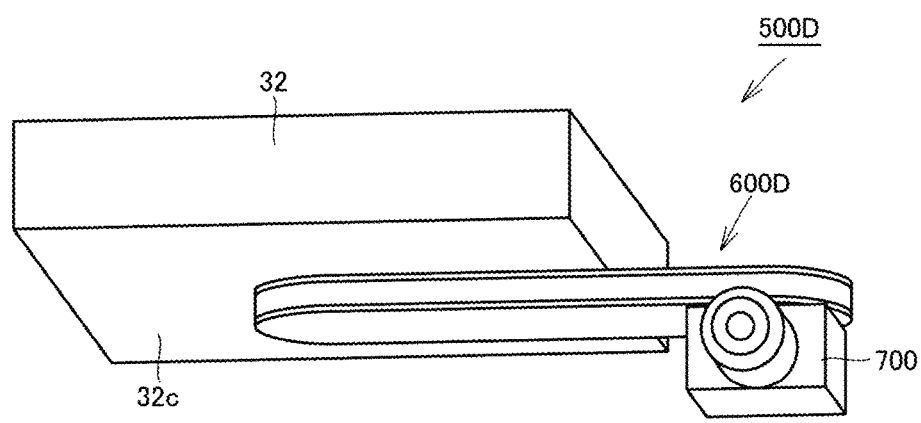
FIG. 24 is a perspective view illustrating a health device flow path formation unit according to a fourth embodiment.
Figure 25:
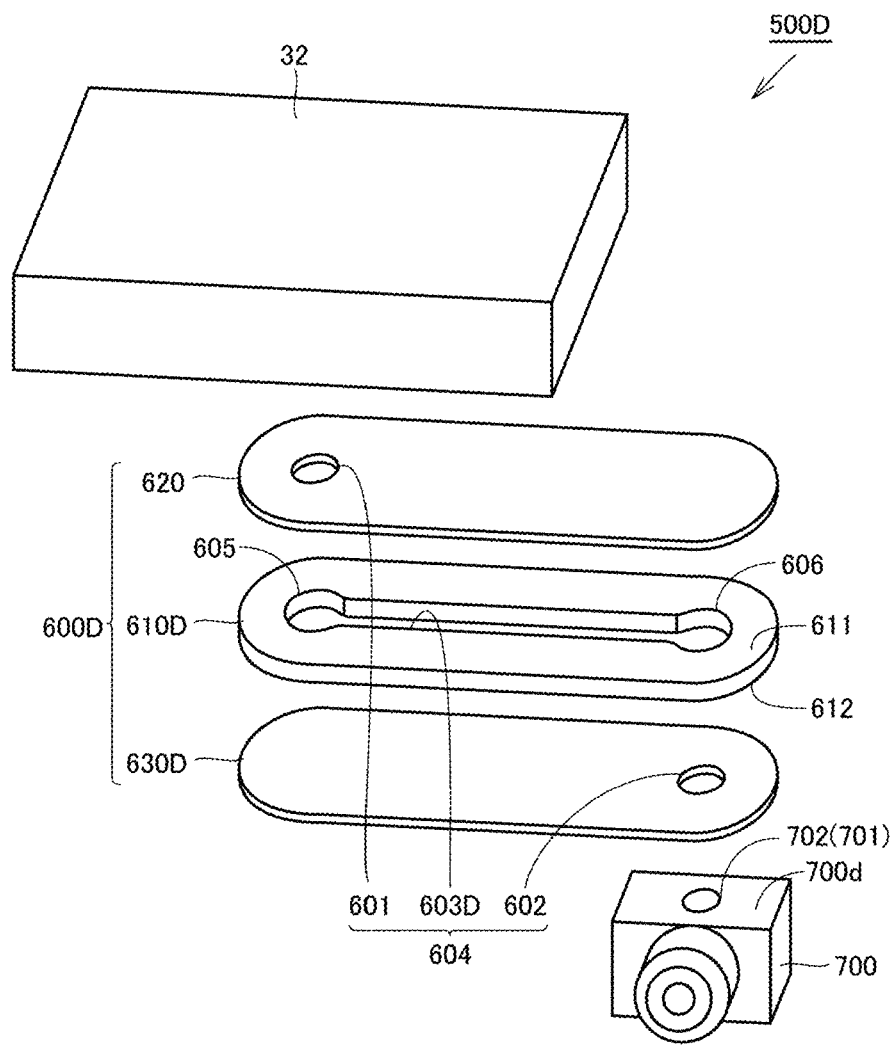
FIG. 25 is an exploded perspective view illustrating the health device flow path formation unit according to the fourth embodiment.
Figure 26:
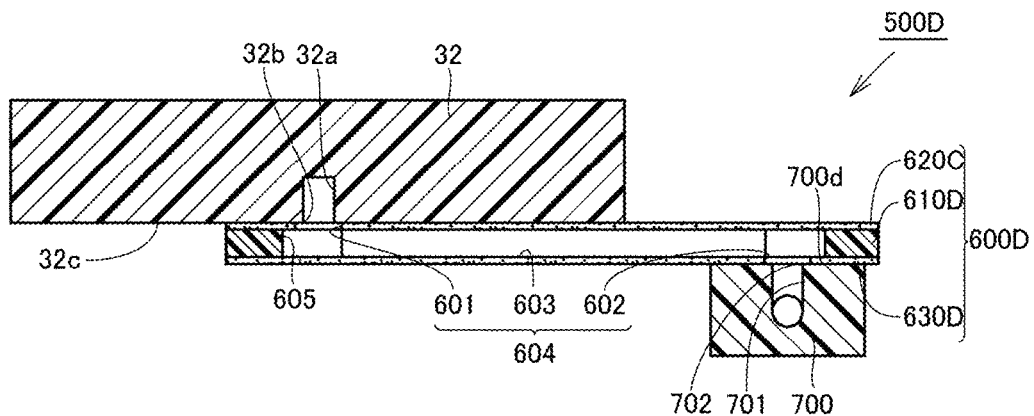
FIG. 26 is a cross-sectional view illustrating the health device flow path formation unit according to the fourth embodiment.

FIG. 24 is a perspective view illustrating a health device flow path formation unit according to a fourth embodiment. FIG. 25 is an exploded perspective view illustrating the health device flow path formation unit according to the fourth embodiment. FIG. 26 is a cross-sectional view illustrating the health device flow path formation unit according to the fourth embodiment. A health device flow path formation unit 500D according to the fourth embodiment will be described with reference to FIGS. 24 to 26.

The health device flow path formation unit 500D according to the fourth embodiment is different from the health device flow path formation unit 500C according to the third embodiment in that the configurations of a plate-like member 610D and a connection layer 630D of a health device flow path formation member 600D are different. Other configurations are substantially similar.

The plate-like member 610D of the health device flow path formation member 600D is different from the plate-like member 610C of the third embodiment in that a connection path 603D opens to both the first main surface 611 and the second main surface 612 in an overall manner. Other configurations are substantially similar.

The connection layer 630D has a different shape from that of the connection layer 630 according to the third embodiment. Other configurations are substantially similar. The connection layer 630D has an elongated shape. The connection layer 630D is disposed on the second main surface 612 covering the connection path 603D except at a portion where the second opening portion 602 overlaps with the connection path 603D in the first direction.

With such a configuration, the health device flow path formation member 600D according to the fourth embodiment can obtain effects similar to that of the health device flow path formation member 600C according to the third embodiment. Also, the health device flow path formation unit 500D and the blood pressure monitor according to the fourth embodiment that include the health device flow path formation member 600D can obtain effects similar to that of the health device flow path formation unit 500C and the blood pressure monitor according to the third embodiment.

Fifth Embodiment

Figure 27:
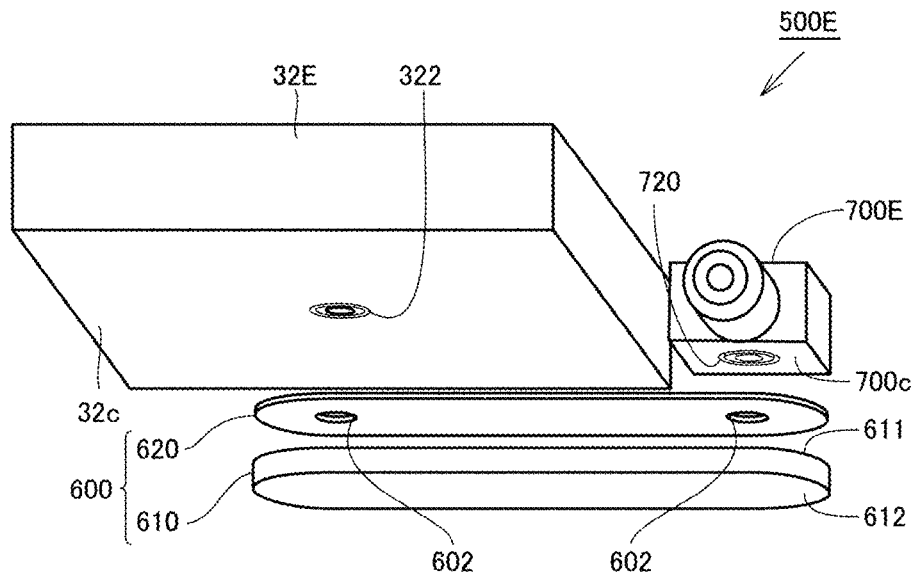
FIG. 27 is an exploded perspective view illustrating a health device flow path formation unit according to a fifth embodiment.
Figure 28:
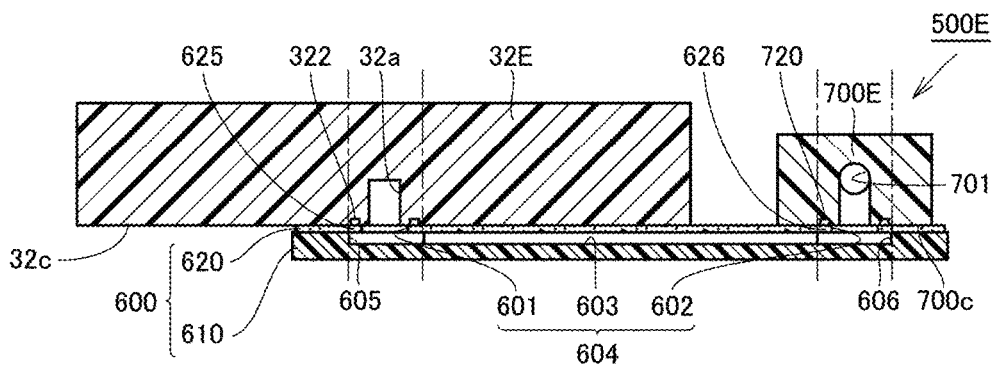
FIG. 28 is a cross-sectional view illustrating the health device flow path formation unit according to the fifth embodiment.

FIG. 27 is an exploded perspective view illustrating a health device flow path formation unit according to a fifth embodiment. FIG. 28 is a cross-sectional view illustrating the health device flow path formation unit according to the fifth embodiment. A health device flow path formation unit 500E according to the fifth embodiment will be described with reference to FIGS. 27 and 28.

As illustrated in FIGS. 27 and 28, the health device flow path formation unit 500E according to the fifth embodiment is different from the health device flow path formation unit 500 according to the first embodiment in that a pump 32E and a connection member 700E have different configurations. Other configurations are substantially similar.

The pump 32E is different from the pump 32 according to the first embodiment in that the pump 32E includes a groove portion 322. The groove portion 322 has an annular shape and is provided in the lower surface 32c of the pump 32E. The groove portion 322 is provided around the first opening portion 601 in a region overlapping the first protrusion portion 625 when viewed in the first direction. The groove portion 322 is recessed in the direction away from the health device flow path formation member 600 in the first direction.

When air is supplied from the pump 32E to the target supply member via the health device flow path formation member 600, a portion of the air supplied from the supply opening 32b of the pump 32E to inside the connection path 603 bounces of the bottom surface portion of the connection path 603, making the first protrusion portion 625 press against the lower surface 32c of the pump 32E.

At this time, a portion of the first protrusion portion 625 enters the groove portion 322 and adheres to the groove portion 322. As a result, the adhesion between the joining layer 620 and the lower surface 32c of the pump 32E can be further increased. Also, by the first protrusion portion 625 pressing against the lower surface 32c, air can be prevented from entering the interface between the joining layer 620 and the lower surface 32c of the pump 32E. As a result, good air tightness is maintained between the health device flow path formation member 600 and the pump 32E.

The connection member 700E is different from the connection member 700 according to the first embodiment in that the connection member 700E includes a groove portion 720. The groove portion 720 has an annular shape and is provided in the lower surface 700c of the connection member 700E. The groove portion 720 is provided around the second opening portion 602 in a region overlapping the second protrusion portion 626 when viewed in the first direction. The groove portion 720 is recessed in the direction away from the health device flow path formation member 600 in the first direction.

When air is supplied from the pump 32 to the target supply member via the health device flow path formation member 600, a portion of the air discharged from the connection path 603 toward an inlet 701a presses the second protrusion portion 626 against the lower surface 700c of the connection member 700E.

At this time, a portion of the second protrusion portion 626 enters the groove portion 720 and adheres to the groove portion 720. As a result, the adhesion between the joining layer 620 and the lower surface 700c of the connection member 700E can be further increased. Also, by the second protrusion portion 626 pressing against the lower surface 700c, air can be prevented from entering the interface between the joining layer 620 and the lower surface 700c of the connection member 700E. As a result, good air tightness is maintained between the health device flow path formation member 600 and the connection member 700E.

With such a configuration, the health device flow path formation unit 500E and a blood pressure monitor provided with the same according to the fifth embodiment can obtain effects similar to that of the health device flow path formation unit 500 and the blood pressure monitor 1 provided with the same according to the first embodiment.

Note that the specific configurations described in the first to fifth embodiments and the first modified example can be combined as appropriate without departing from the spirit of the present invention.

In addition, in the first to fifth embodiments and the first modified example, a pump is provided on the first opening portion 601 side of the health device flow path formation member and a connection member is disposed on the second opening portion 602 side of the health device flow path formation member. However, no such limitation is intended, and the connection member may be disposed on the first opening portion 601 side, and the pump may be disposed on the second opening portion 602 side. Also, in at least embodiment, the second target placement member is the connection member. However, no such limitation is intended, and the second target placement member may be the target supply member which fluid is goes in and out of.

The health device flow path formation member according to an embodiment of the present disclosure described above includes:
  a flow path configured to supply fluid to a target supply member;
  a first opening portion located at a first end of the flow path;
  a second opening portion located at a second end of the flow path;
  a connection path connecting the first opening portion and the second opening portion;
  a plate-like member including the connection path; and
  a joining layer including at least the first opening portion of the first opening portion and the second opening portion, the joining layer joining the plate-like member to a first target attachment member with the first opening portion communicating with a fluid path of the first target attachment member. When viewed in a first direction in which the joining layer and the plate-like member overlap, the first opening portion is disposed inward a distance from a profile line of a projection of the connection path in the first direction, forming a first protrusion portion in the joining layer that protrudes inward from the profile line.

In the health device flow path formation member according to an embodiment of the present disclosure described above, the connection path may include a main path portion provided inside the plate-like member, a first auxiliary path portion connecting the first opening portion and the main path portion, and a second auxiliary path portion connecting the second opening portion and the main path portion. In this embodiment, when viewed in the first direction, the first auxiliary path portion is preferably disposed inward from the main path portion, forming a first projection portion in the plate-like member that defines the first auxiliary path portion and projects inward from the main path portion; and
  the first protrusion portion is preferably supported by the first projection portion.

In the health device flow path formation member according to an embodiment of the present disclosure described above, the second opening portion may be disposed in the joining layer.

In the health device flow path formation member according to an embodiment of the present disclosure described above, when viewed in the first direction, the second opening portion may be disposed inward a distance from the profile line of the projection, forming a second protrusion portion in the joining layer that protrudes inward from the profile line.

The health device flow path formation member according to an embodiment of the present disclosure described above may further include a connection layer including the second opening portion, the connection layer connecting the plate-like member to a second target attachment member with the second opening portion communicating with a fluid path of the second target attachment member. In this embodiment, the plate-like member preferably includes a first main surface and a second main surface that are front and back surfaces in the first direction. Also, the joining layer is preferably disposed on a side of the plate-like member where the first main surface is located, and the connection layer is preferably disposed on a side of the plate-like member where the second main surface is located.

In the health device flow path formation member according to an embodiment of the present disclosure described above, when viewed in the first direction, the second opening portion is preferably disposed inward a distance from the profile line of the projection of the connection path in the first direction, forming a second protrusion portion in the connection layer that protrudes inward from the profile line.

In the health device flow path formation member according to an embodiment of the present disclosure described above, the connection path preferably includes a tapered portion at a portion located at the first end, the tapered portion tapering becoming thinner in the first direction in a direction away from the joining layer.

A health device flow path formation member according to an embodiment of the present disclosure includes:
- a flow path configured to supply fluid to a target supply member;
- a first opening portion located at a first end of the flow path;
- a second opening portion located at a second end of the flow path;
- a connection path connecting the first opening portion and the second opening portion;
- a plate-like member including the connection path; and
- a joining layer including at least the first opening portion of the first opening portion and the second opening portion, the joining layer joining the plate-like member to a first target attachment member with the first opening portion communicating with a fluid path of the first target attachment member. When viewed in a first direction in which the joining layer and the plate-like member overlap, the first opening portion is disposed inward a distance from a profile line of a projection of the connection path in the first direction, forming a first protrusion portion in the joining layer that protrudes inward from the profile line. The second opening portion is disposed in the joining layer. The plate-like member includes a first main surface and a second main surface that are front and back surfaces in the first direction. The connection path has an opening shape that opens to the first main surface. The joining layer is disposed on the first main surface covering the connection path except at a portion where the first opening portion and the second opening portion overlap with the connection path in the first direction.

A health device flow path formation member according to an embodiment of the present disclosure includes:
- a flow path configured to supply fluid to a target supply member;
- a first opening portion located at a first end of the flow path;
- a second opening portion located at a second end of the flow path;
- a connection path connecting the first opening portion and the second opening portion;
- a plate-like member including the connection path; and
- a joining layer including at least the first opening portion of the first opening portion and the second opening portion, the joining layer joining the plate-like member to a first target attachment member with the first opening portion communicating with a fluid path of the first target attachment member. When viewed in a first direction in which the joining layer and the plate-like member overlap, the first opening portion is disposed inward a distance from a profile line of a projection of the connection path in the first direction, forming a first protrusion portion in the joining layer that protrudes inward from the profile line. The health device flow path formation member described above further includes a connection layer including the second opening portion, the connection layer connecting the plate-like member to a second target attachment member with the second opening portion communicating with a fluid path of the second target attachment member. The plate-like member includes a first main surface and a second main surface that are front and back surfaces in the first direction. The joining layer is disposed on a side of the plate-like member where the first main surface is located, and the connection layer is disposed on a side of the plate-like member where the second main surface is located. The connection path has an opening shape that opens to the first main surface. The joining layer is disposed on the first main surface covering the connection path except at a portion where the first opening portion overlaps with the connection path in the first direction.

A health device flow path formation member according to an embodiment of the present disclosure includes:
- a flow path configured to supply fluid to a target supply member;
- a first opening portion located at a first end of the flow path;
- a second opening portion located at a second end of the flow path;
- a connection path connecting the first opening portion and the second opening portion;
- a plate-like member including the connection path; and
- a joining layer including at least the first opening portion of the first opening portion and the second opening portion, the joining layer joining the plate-like member to a first target attachment member with the first opening portion communicating with a fluid path of the first target attachment member. The connection path includes a main path portion provided inside the plate-like member, a first auxiliary path portion connecting the first opening portion and the main path portion, and a second auxiliary path portion connecting the second opening portion and the main path portion. When viewed in the first direction, the first auxiliary path portion is disposed inward from the main path portion, forming a first projection portion in the plate-like member that defines the first auxiliary path portion and projects inward from the main path portion. The first protrusion portion is supported by the first projection portion. The second opening portion is disposed in the joining layer. When viewed in the first direction, the second opening portion is disposed inward a distance from the profile line of the projection, forming a second protrusion portion in the joining layer that protrudes inward from the profile line. When viewed in the first direction, the second auxiliary path portion is disposed inward from the main path portion, forming a second projection portion in the plate-like member that defines the second auxiliary path portion and projects inward from the main path portion. The second protrusion portion is supported by the second projection portion.

A health device flow path formation member according to an embodiment of the present disclosure includes:
- a flow path configured to supply fluid to a target supply member;
- a first opening portion located at a first end of the flow path;
- a second opening portion located at a second end of the flow path;
- a connection path connecting the first opening portion and the second opening portion;
- a plate-like member including the connection path; and
- a joining layer including at least the first opening portion of the first opening portion and the second opening portion, the joining layer joining the plate-like member to a first target attachment member with the first opening portion communicating with a fluid path of the first target attachment member. The connection path includes a main path portion provided inside the plate-like member, a first auxiliary path portion connecting the first opening portion and the main path portion, and a second auxiliary path portion connecting the second opening portion and the main path portion. When viewed in the first direction, the first auxiliary path portion is disposed inward from the main path portion, forming a first projection portion in the plate-like member that defines the first auxiliary path portion and projects inward from the main path portion. The first protrusion portion is supported by the first projection portion. When viewed in the first direction, the second opening portion is disposed inward a distance from the profile line of the projection, forming a second protrusion portion in the connection layer that protrudes inward from the profile line. When viewed in the first direction, the second auxiliary path portion is disposed inward from the main path portion, forming a second projection portion in the plate-like member that defines the second auxiliary path portion and projects inward from the main path portion; and
the second protrusion portion is supported by the second projection portion.

A health device flow path formation unit according to an embodiment of the present disclosure includes:
- the health device flow path formation member described above; and
- the first target attachment member on which the health device flow path formation member is attached.

In the health device flow path formation unit according to an embodiment of the present disclosure described above, the first target attachment member preferably includes a first target attachment surface on which the health device flow path formation member is attached. In this embodiment, the first target attachment surface preferably includes a groove portion provided around the first opening portion in a region overlapping the first protrusion portion when viewed in the first direction, the groove portion being recessed in a direction away from the health device flow path formation member in the first direction.

In the health device flow path formation unit according to an embodiment of the present disclosure described above, the first target attachment member is preferably a fluid supply source that supplies fluid.

The health device flow path formation unit according to an embodiment of the present disclosure described above preferably further includes the second target attachment member on which the health device flow path formation member is attached, with the second opening portion communicating with the fluid path of the second target attachment member.

In the health device flow path formation unit according to an embodiment of the present disclosure described above, the second target attachment member is preferably a connection member through which fluid is supplied from the health device flow path formation member to a target supply member.

A health device according to an embodiment of the present disclosure includes:
- the health device flow path formation unit; and
- a fluid bag into which fluid is supplied from the health device flow path formation unit.

The embodiments described herein are illustrative in all respects and are not intended as limitations. The scope of the present invention is indicated by the claims and includes all meaning equivalent to the scope and changes within the scope.

REFERENCE SIGNS LIST

1 Wrist blood pressure monitor
10 Body
10b Bottom surface
15 Buckle
20 Belt
20a Inner circumferential surface
20b Outer circumferential surface
20e, 20f End portion
21 Compression cuff
21a Outer circumferential surface
22 Solid material
23 Band
23a Inner circumferential surface
24 Pressing cuff
24a Inner circumferential surface
25 First plate-like member
25e, 25f End portion
26 Second plate-like member
26e, 26f End portion
27, 28 Connecting rod
29 Fixing portion
31 First pressure sensor
32, 32E, 32X Pump
32a Fluid path
32b Supply opening
32c Lower surface
33 Valve
34 Second pressure sensor
35 Switching valve
38a, 38b, 39a, 39b Air line
40 Impedance measurement portion
40E Electrode group
41, 42, 43, 44, 45, 46 Electrode
49 Voltage detection circuit
50 Display
51 Memory
52 Operation portion 53 Battery
59 Communication unit
71, 72 Wire
90 Left wrist
90a Palm side surface
91 Radial artery
310 Oscillation circuit
320 Pump drive circuit
321 Nozzle
322 Groove portion
340 Oscillation circuit
401 First pulse wave sensor
402 Second pulse wave sensor
500, 500A, 500B, 500C, 500D, 500E, 500X Health device flow path formation unit
600, 600A, 600B, 600C, 600D, 600X Health device flow path formation member
601 First opening portion
602 Second opening portion
603, 603B, 603D Connection path
604 Flow path
605 First chamber
606, 606C Second chamber
610, 610B, 610C, 610D Plate-like member
610B1 First portion
610B2 Second portion
611 First main surface
612 Second main surface
615 First projection portion
616 Second projection portion
620, 620C Joining layer
625 First protrusion portion
626 Second protrusion portion
630, 630D Connection layer
636 Second protrusion portion
651, 652 Bend portion
700, 700E, 700X Connection member
700c Lower surface
700d Upper surface
701 Fluid path
702 Inlet
711 Nozzle
720 Groove portion
900 Network
6030 Main path portion
6031 First auxiliary path portion
6032 Second auxiliary path portion

The invention claimed is:

1. A health device flow path formation member connected to a pump, which is provided as a fluid supply source, comprising:
a flow path configured to supply fluid to a target supply member;
a first opening located at a first end of the flow path;
a second opening located at a second end of the flow path;
a connection path connecting the first opening and the second opening;
a plate-like member comprising the connection path; and
a first adhesive layer comprising at least the first opening or the first opening and the second opening, the first adhesive layer including a first adhesion surface and a second adhesion surface for adhering the plate-like member to the first adhesion surface and for adhering the pump to the second adhesion surface so that the first opening communicates with a fluid path of the pump,
wherein when viewed in a first direction in which the first adhesive layer and the plate-like member overlap, the first opening is disposed inward a distance from a profile line of a projection of the connection path in the first direction, forming a first protrusion in the first adhesive layer that protrudes inward from the profile line and against a lower surface of the pump;
the connection path comprises a main path provided inside the plate-like member, a first auxiliary path connecting the first opening and the main path, and a second auxiliary path connecting the second opening and the main path;
when viewed in the first direction, the first auxiliary path is disposed inward from the main path, forming a first projection in the plate-like member that defines the first auxiliary path and projects inward from the main path;
the first protrusion is supported by the first projection;
the plate-like member includes a first portion and a second portion;
the first portion is located on one side of the plate-like member in a thickness direction and provided with a through hole that becomes the first auxiliary path;
the second portion is located on the other side of the plate-like member in the thickness direction and includes a groove portion that opens toward the one side in the thickness direction;
the groove defines the main path; and
the first opening located at the first end of the flow path and the second opening located at the second end of the flow path each have a larger diameter than the connection path.

2. The health device flow path formation member according to claim 1,
wherein the second opening is disposed in the first adhesive layer.

3. The health device flow path formation member according to claim 2,
wherein when viewed in the first direction, the second opening is disposed inward a distance from the profile line of the projection, forming a second protrusion in the first adhesive layer that protrudes inward from the profile line.

4. The health device flow path formation member according to claim 1, further comprising:
a second adhesive layer comprising the second opening, the second adhesive layer adhering the plate-like member to a target attachment member different from the pump with the second opening portion communicating with a fluid path of the target attachment member,
wherein the plate-like member comprises a first main surface and a second main surface that are front and back surfaces in the first direction;
the first adhesive layer is disposed on a side of the plate-like member where the first main surface is located; and
the second adhesive layer is disposed on a side of the plate-like member where the second main surface is located.

5. The health device flow path formation member according to claim 4,
wherein when viewed in the first direction, the second opening is disposed inward a distance from the profile line of the projection, forming a second protrusion in the second adhesive layer that protrudes inward from the profile line.

6. The health device flow path formation member according to claim 1, wherein the connection path comprises a tapered end located at the first end, the tapered end tapering so as to become thinner in the first direction in a direction away from the first adhesive layer.

7. A health device flow path formation device, comprising:
    the health device flow path formation member according to claim 1; and
    the pump on which the health device flow path formation member is attached.

8. The health device flow path formation device according to claim 7,
    wherein the pump comprises a first target attachment surface on which the health device flow path formation member is attached; and
    the first target attachment surface comprises a groove provided around the first opening in a region overlapping the first protrusion when viewed in the first direction, the groove being recessed in a direction away from the health device flow path formation member in the first direction.

9. The health device flow path formation device according to claim 7, further comprising
    a target attachment member different from the pump on which the health device flow path formation member is placed with the second opening communicating with a fluid path of the target attachment member.

10. The health device flow path formation device according to claim 9,
    wherein target attachment member is a connection through which fluid is supplied from the health device flow path formation member to a target supply member.

11. A health device, comprising:
    the health device flow path formation device according to claim 7; and
    a fluid bag into which fluid is supplied from the health device flow path formation unit.

* * * * *